United States Patent [19]

Hediger

[11] Patent Number: 5,441,875
[45] Date of Patent: Aug. 15, 1995

[54] UREA TRANSPORTER POLYPEPTIDE

[75] Inventor: Matthias A. Hediger, Brookline, Mass.

[73] Assignee: Brigham and Women's Hospital, Boston, Mass.

[21] Appl. No.: 98,141

[22] Filed: Jul. 23, 1993

[51] Int. Cl.⁶ ............................................... C12P 21/06
[52] U.S. Cl. ........................................ 435/69.1; 435/6; 435/71.1; 435/172.3; 435/320.1; 435/91; 536/23.1; 536/23.5; 536/24.3; 536/24.31
[58] Field of Search .................... 435/6, 69.1, 71.1, 91, 435/172.3, 317.1; 536/23.1, 23.5, 24.3, 24.31; 424/557

[56] References Cited

PUBLICATIONS

R. Zhang, et al., "Urea Transport in Freshly Isolated and Cultured Cells from Rat Inner Medullary Collecting Duct", 1990, *J. Membrane Biol.*, vol. 117, pp. 253–261.

M. Hediger, et al., "Expression Cloning and cDNA Sequencing of the Na+/glucose Co-Transporter", Nov. 1987, *Nature*, vol. 330, No. 26, pp. 379–381.

M. Hediger, et al., "Expression of Size-Selected mRNA Encoding the Intestinal Na/glucose Cotransporter in *Xenopus Laevis* Oocytes", May 1987, *Proc. Natl. Acad. Sci. USA*, vol. 84, pp. 2634–2637.

Chou, C-L, et al., "Inhibition of Urea Transport in Inner Medullary Collecting Duct by Phloretin and Urea Analogues", May 1989, *Natl. Heart, Lung, and Blood Inst.*, Bethesda, Md., pp. F359–F365.

R. Zhang, et al., "Water and Urea Permeability Properties of Xenopus Oocytes: Expression of mRNA from Toad Urinary Bladder"; 1991, *Amer. Physiological Society*, pp. C26–C34.

*Primary Examiner*—Christine M. Nucker
*Assistant Examiner*—Laurie Scheiner
*Attorney, Agent, or Firm*—Choate, Hall & Stewart

[57] ABSTRACT

An isolated nucleotide sequence encoding a urea transporter polypeptide or unique fragments of urea transporter polypeptide, is provided. One embodiment is an isolated DNA sequence (SEQ ID NO.:1) encoding a urea transporter polypeptide, that has at least two extended hydrophobic domains, each domain lacking interspersed hydrophilic domains. Also described are recombinant cells and plasmids containing the foregoing isolated DNA, preferably linked to a promoter. Isolated urea transporter polypeptide is provided, having at least two extended hydrophobic domains, each domain lacking interspersed hydrophilic domains (SEQ ID NO.:2). Portions of the foregoing isolated urea transporter polypeptides are also described. Antibodies with selective binding specificity for the polypeptides of the invention also are provided.

Methods for producing urea transporter polypeptide as well as methods for testing for modulators of urea transporter polypeptide activity are also described.

9 Claims, 6 Drawing Sheets

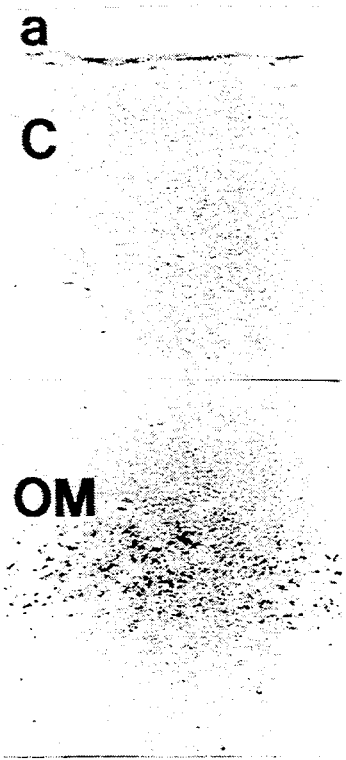
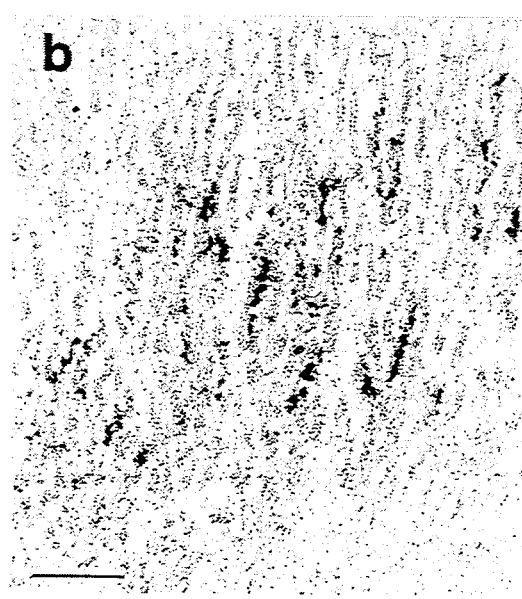
FIG. 7b
FIG. 7c
FIG. 7a

5,441,875

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3060 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

```
CCCACGCGTC  CGAGAGACCT  TTCTGGATAC  AGGGGTTAGG  CCACACCCTT  CTTGCTCTGA      60
GAGGGTCCCC  ATCAGCCCCC  AAGACCCTGG  TCAGCAGGAT  TTAGCAGGAA  AGGTTGGAAA     120
TTTTCCATAG  AACCAGAAAG  ACACCATCTA  GCATGGGGCT  GGTGCCAAAC  TTTCCACCAA     180
GACGCTGATG  GCAGTGTTGA  TCCCCAGGCT  GTGCCTGGCC  TGCACAAGGA  ATTAAGGGAG     240
CTTACTGAGG  TTGGAAGGCA  AATTGACCTC  ATAAGGAGAA  AACACGTAGA  TAATAGCTTG     300
AAAGGCAAGT  CCTGGAGCTA  GAATTCTAAT  GAGAGGAGGT  AATGCCTGAG  AGACTACAGG     360
GAAGCTGCTA  GACAGTCCCC  AGCTCCACCC  TTTAAGGAA   ACCTGCCAAG  TCCACCCAGG     420
TTGGGAGGGG  GGAACCATGG  TAGTTAGAGC  TCTTCTTGCC  CAAGGAGATT  AGAAAAGAGA     480
CTTGGGGTAC  AGAGGCCACA  GGGACGTGGG  AGAGCTCCAG  AAGGGGCATT  TGTCTTTCTC     540
CTCCCTCCTC  CTCTTCCATG  GTGCTCTTCC  TCGGCTGGCA  GACATGCACT  GGGCATAGGC     600
TTAGGGGATG  CAAGTCAGTG  AGGTTACAGA  AAGTTGGCAA  GAGGATGGAC  TGGAGGCCTG     660
AAGGAAGTGA  AAGATTTCAG  GTTTAGGAGG  AGTCCCGCG   TCTGGAGTTG  AGGACCAGAG     720
ACGCCTTCCA  GTCGGAAGGA  AGCCTCTTCC  CAAGCCCTGA  TGGTCTAGAT  TCCTCCAGCC     780
CTGTGCAGGA  AGCCAAAAGG  AGCCCAGGCG  GCGGCGGGGA  GCAGCCACCA  GCAGCCGGCC     840
TGAAGGCCGA  GGAGGGCTCA  GAGCCTGCGG  CCCCAAGCCC  AGGAGCGTGT  TCCACATCGA     900
GTGGTCATCT  ATACGGAGGA  GGAGCAAAGT  GTTTGGGAAA  GGCGAGCAGC  AGGAGAGACA     960
GCCCAAGGTG  CCCCTTCCCT  ATCAATACCG  GAAGCCCTCG  GTGGAACTGC  TTAATCTGGG    1020
CCCCATGGAG  GACAGCTCTG  AGATAAAGGT  GGAGACCGCC  AGCTCCAGGA  CTTCCTGGAT    1080
CCAGAGTTCC  GTGGCTGCTG  GTGGGAAAAG  GATCAGCAGG  GCCCTCGGCT  ACATCACCGG    1140
GGAGATGAAG  GAGTGTGCAG  AGGGGCTTAA  AGACAAGTCC  CCCGTGTTCC  AGTTCCTCGA    1200
CTGGGTTCTC  CGAGGCACAT  CTCAGGTGAT  GTTTGTGAAC  AACCCCCTCA  GTGGCATCCT    1260
CATCGTGATT  GGCCTCTTTG  TCCAGAACCC  ATGGTGGGCC  ATCGCGGGAT  GCCTGGGCAC    1320
CGTCATGTCC  ACCTTGACTG  CCCTCATCCT  GAGCCAGGAC  AGGTCAGCCA  TCGCCTCCGG    1380
```

| | | | | | |
|---|---|---|---|---|---|
| ACTCCACGGC | TACAACGGCG | TGCTGGTGGG | GCTGCTGATA | GCCGTGTTCT | CCGACAAGGG | 1440 |
| CGACTATTAC | TGGTGGCTTC | TGCTCCCTGT | CATCGTGATG | TCCATGTCCT | GCCCCATCCT | 1500 |
| CTCCAGTGCC | CTGGGCACCA | TCTTCAGCAA | GTGGGACCTC | CCAGTCTTCA | CACTGCCCTT | 1560 |
| CAACATCGCC | GTGACCCTGT | ACCTGGCAGC | CACAGGCCAC | TACAACCTCT | TCTTCCCCAC | 1620 |
| AACACTGCTG | CAGCCTGTAT | CCTCCGTGCC | CAACATCACC | TGGTCAGAGA | TCCAGGTGCC | 1680 |
| CTTGCTCTTG | AGAGCCATCC | CCGTTGGAAT | CGGCCAAGTG | TATGGCTGTG | ATAACCCCTG | 1740 |
| GACTGGAGGC | ATTTTCCTCA | TCGCTCTGTT | CATATCTTCA | CCTCTTATTT | GCTTGCATGC | 1800 |
| GGCAATTGGA | TCCACCATGG | GGATGTTAGC | AGCACTCACG | ATTGCCACAC | CCTTTGACTC | 1860 |
| CATCTACTTT | GGCCTGTGTG | GCTTCAACAG | CACGCTGGCA | TGCATCGCTG | TCGGAGGCAT | 1920 |
| GTTCTACGTC | ATCACCTGGC | AGACTCACCT | CCTTGCTGTT | GCCTGCGCCC | TGTTTGCGGC | 1980 |
| CTACGTGGGT | GCTGCCCTGA | CCAACGTATT | ATCTGTGTTT | GGATTACCAA | CCTGCACCTG | 2040 |
| GCCCTTCTGC | ATCTCAGCAC | TCATCTTCCT | GCTCCTGACG | ACCAACAACC | CTGCCATCTA | 2100 |
| CAAACTCCCG | CTCAGCAAAG | TCACCTACCC | AGAAGCCAAC | CGCACCTACT | ACCTGACCCA | 2160 |
| GGAGAGAAAC | AGAAGGTCAT | CAACCATAAC | GAAGTATCAG | GCCTACGATG | TCTCCTAAGT | 2220 |
| TACCCTTTCC | AAAACACTGG | AAATTCAGCC | TTCACGAGGC | TGCCCGGGTC | CCCAGGCCAA | 2280 |
| AAGCCACCCA | ACCTCCCCTC | CTGACTATTC | TGTGATTCTC | CCCTACCCCT | GCCAATCAAG | 2340 |
| CCTCCACCAC | AGTTCTTCCC | AAACACAGGG | AAACATGTGT | GGTCACCATT | TAAGAAGCTC | 2400 |
| TCCCTTCTTA | AATGCACAAC | CCTTATCAGA | TATGTTAGAC | TTTGTACCCA | TAGCTGGGCC | 2460 |
| TATAAGAGCT | CCTGTTGTGA | AGAACTTGCC | CTCTTCTGCA | AAGAAGTGT | CCTATGTACA | 2520 |
| GGGAAGTCCC | CAAGGAGAGG | GCAGAGATGG | GTGATATGGT | CACTGAGTAT | AGCAAAGCCC | 2580 |
| AGTGCCAGGA | AATGTGCCTG | GGCCTGGCAG | GCAAGGGCTG | GGTTCTGCTC | CTGGCTCCAC | 2640 |
| TAGGTCCTTT | CCCACTCAGC | CTTGATTTCT | GCCTGGCAGG | GATTTCTTCA | CGACAGGGAG | 2700 |
| GGTCTCCAAA | GTCCCTTCGA | CTCTAGAACT | GTTGATTCTC | TCTCCTATAA | ACTGATGAAA | 2760 |
| TCAGTGTTGA | CCAGTAATTG | CCTTAAGGAA | AAGATAGAAG | GGTTACCCTG | AGAAGAGGCA | 2820 |
| GAAAAAATG | TTAATGTTCC | ATGCAGGGTT | ATTCTTGGAT | GATGGGAAGA | TACTCTTCAG | 2880 |
| ATTTGGGGTT | AAGAACCTAA | ATTCACTGAC | AACGCCAATG | TGCCTTCCTT | TACATAACAC | 2940 |
| AAACATTGCT | GGAAATGTCC | TTAGAAACTG | ATTTTTTTCA | GCATTCAAAT | CACATTGTAA | 3000 |
| ACAAATGCCT | TTCCTTTTGT | TGTATTCATA | ATCATGCTGT | CATTAAAGTG | TTTAAGGATG | 3060 |

( 2 ) INFORMATION FOR SEQ ID NO:2:

( i ) SEQUENCE CHARACTERISTICS:
( A ) LENGTH: 397 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Glu Asp Ser Ser Glu Ile Lys Val Glu Thr Ala Ser Ser Arg Thr
 1               5                  10                  15

Ser Trp Ile Gln Ser Ser Val Ala Ala Gly Gly Lys Arg Ile Ser Arg
            20                  25                  30

Ala Leu Gly Tyr Ile Thr Gly Glu Met Lys Glu Cys Ala Glu Gly Leu
        35                  40                  45

Lys Asp Lys Ser Pro Val Phe Gln Phe Leu Asp Trp Val Leu Arg Gly
    50                  55                  60

Thr Ser Gln Val Met Phe Val Asn Asn Pro Leu Ser Gly Ile Leu Ile
```

|  65 | | | | | 70 | | | | | 75 | | | | | 80 |
|---|---|---|---|---|---|---|---|---|---|---|---|---|---|---|---|
| Val | Ile | Gly | Leu | Phe 85 | Val | Gln | Asn | Pro | Trp 90 | Trp | Ala | Ile | Ala 95 | Gly | Cys |
| Leu | Gly | Thr | Val 100 | Met | Ser | Thr | Leu | Thr 105 | Ala | Leu | Ile | Leu | Ser 110 | Gln | Asp |
| Arg | Ser | Ala 115 | Ile | Ala | Ser | Gly | Leu 120 | His | Gly | Tyr | Asn | Gly 125 | Val | Leu | Val |
| Gly | Leu 130 | Leu | Ile | Ala | Val | Phe 135 | Ser | Asp | Lys | Gly | Asp 140 | Tyr | Tyr | Trp | Trp |
| Leu 145 | Leu | Leu | Pro | Val | Ile 150 | Val | Met | Ser | Met | Ser 155 | Cys | Pro | Ile | Leu | Ser 160 |
| Ser | Ala | Leu | Gly | Thr 165 | Ile | Phe | Ser | Lys | Trp 170 | Asp | Leu | Pro | Val | Phe 175 | Thr |
| Leu | Pro | Phe | Asn 180 | Ile | Ala | Val | Thr | Leu 185 | Tyr | Leu | Ala | Ala | Thr 190 | Gly | His |
| Tyr | Asn | Leu 195 | Phe | Phe | Pro | Thr | Thr 200 | Leu | Leu | Gln | Pro | Val 205 | Ser | Ser | Val |
| Pro | Asn 210 | Ile | Thr | Trp | Ser | Glu 215 | Ile | Gln | Val | Pro | Leu 220 | Leu | Leu | Arg | Ala |
| Ile 225 | Pro | Val | Gly | Ile | Gly 230 | Gln | Val | Tyr | Gly | Cys 235 | Asp | Asn | Pro | Trp | Thr 240 |
| Gly | Gly | Ile | Phe | Leu 245 | Ile | Ala | Leu | Phe | Ile 250 | Ser | Ser | Pro | Leu | Ile 255 | Cys |
| Leu | His | Ala | Ala 260 | Ile | Gly | Ser | Thr | Met 265 | Gly | Met | Leu | Ala | Ala 270 | Leu | Thr |
| Ile | Ala | Thr 275 | Pro | Phe | Asp | Ser | Ile 280 | Tyr | Phe | Gly | Leu | Cys 285 | Gly | Phe | Asn |
| Ser | Thr 290 | Leu | Ala | Cys | Ile | Ala 295 | Val | Gly | Gly | Met | Phe 300 | Tyr | Val | Ile | Thr |
| Trp 305 | Gln | Thr | His | Leu | Leu 310 | Ala | Val | Ala | Cys | Ala 315 | Leu | Phe | Ala | Ala | Tyr 320 |
| Val | Gly | Ala | Ala | Leu 325 | Thr | Asn | Val | Leu | Ser 330 | Val | Phe | Gly | Leu | Pro 335 | Thr |
| Cys | Thr | Trp | Pro 340 | Phe | Cys | Ile | Ser | Ala 345 | Leu | Ile | Phe | Leu | Leu 350 | Leu | Thr |
| Thr | Asn | Asn 355 | Pro | Ala | Ile | Tyr | Lys 360 | Leu | Pro | Leu | Ser | Lys 365 | Val | Thr | Tyr |
| Pro | Glu 370 | Ala | Asn | Arg | Thr | Tyr 375 | Tyr | Leu | Thr | Gln | Glu 380 | Arg | Asn | Arg | Arg |
| Ser 385 | Ser | Thr | Ile | Thr | Lys 390 | Tyr | Gln | Ala | Tyr | Asp 395 | Val | Ser | | | |

UREA TRANSPORTER POLYPEPTIDE

This invention was made with U.S. Government Support under National Institutes of Health Grant No. NIH: DK 43171. The U.S. Government has certain rights to this invention.

BACKGROUND OF THE INVENTION

Urea is the major end product of nitrogen metabolism in mammals. In the kidney, urea transport plays a central role in the urinary concentration mechanism and in water conservation. Transport of urea, regulated by vasopressin, is via a facilitated transporter located in the inner medulla collecting duct ("IMCD") of the kidney. Urea transporters situated in the plasma membranes of other epithelia including colon, liver, and lung, are crucial for urea and nitrogen metabolism.

It has been very difficult to obtain reliable information about the identity of urea transporters. There are presently no known effective urea transport inhibitors. Furthermore, urea transporters are very hydrophobic, making them hard to isolate and purify.

SUMMARY OF THE INVENTION

According to one aspect of the invention, an isolated nucleotide sequence encoding a urea transporter polypeptide or unique fragments of urea transporter polypeptide, is provided. One embodiment is an isolated DNA sequence encoding a urea transporter polypeptide, that has at least two extended hydrophobic domains, each domain lacking interspersed hydrophilic domains. Additionally, the invention relates to vertebrate urea transporter nucleotide sequences isolated from porcine, ovine, bovine, feline, avian, equine, or canine, as well as primate (e.g. human) sources.

Also provided are recombinant cells and plasmids containing the foregoing isolated DNA, preferably linked to a promoter. Portions of the foregoing nucleotide sequences are also included in the invention. One such portion is contained in a vector within a host cell.

According to another aspect of the invention, isolated urea transporter polypeptide is provided, having at least two extended hydrophobic domains, each domain lacking interspersed hydrophilic domains. The isolated polypeptide of the invention has a variety of functional properties including the ability to facilitate urea transport across a cell membrane in a manner that is: (i) substantially independent of sodium and chloride ion concentration; and (ii) substantially inhibited by urea analogues and/or phloretin.

Portions of the foregoing isolated urea transporter polypeptides are also included in the invention. Antibodies with selective binding specificity for the polypeptides of the invention also are provided.

Another aspect of the invention is a method for producing urea transporter polypeptide. The method includes providing an expression vector to a host, the vector containing a DNA sequence of the invention encoding for urea transporter polypeptide, allowing the host to express the urea transporter polypeptide, and isolating the expressed urea transporter polypeptide.

A further aspect of the invention is an isolated nucleotide sequence capable of hybridizing to a target nucleotide sequence encoding urea transporter polypeptide. The target includes a nucleotide sequence encoding a urea transporter polypeptide with at least two extended hydrophobic domains, each domain lacking interspersed hydrophilic domains. The nucleotide sequence also can encode a urea transporter polypeptide having sequences unique to the polypeptide.

Also provided is a urea transporter polypeptide having a restricted range of expression in tissues. The preferred polypeptide is phloretin-inhibitable and is expressed in mammalian tissue selected from the group consisting of mammalian renal papillary tip, renal inner and outer medulla, colon, liver, and lung tissue. Related sequences are expressed in mammalian cerebrum and cerebellum tissue.

The novel molecules of the invention can be employed in experimental or therapeutic protocols. For example, a method for interfering with the activity of a urea transporter gene may be accomplished by providing a construct arranged to include a urea transporter nucleotide sequence which, when inserted, inactivates either transcription of messenger RNA for urea transporter polypeptide and/or inactivates translation of messenger RNA into urea transporter polypeptide. This construct further has a promotor operatively linked to the sequence. Next, the construct is introduced into a cell, and the construct is allowed to recombine with complementary sequences of the cell genome. Finally, cells lacking the ability to express urea transporter polypeptide are selected.

A further aspect of the invention is an assay method for identifying a modulator of a urea transporter polypeptide. The method includes providing a target cell containing an isolated nucleotide sequence which encodes for a urea transporter polypeptide. The target cell is maintained under conditions and for a time sufficient for the urea transporter polypeptide to be expressed in the target cell. The target cell is then exposed to a compound suspected of modulating urea transporter polypeptide activity and a property of the target cell is measured in the presence of the modulator. This property is also measured in an identical target cell in the absence of the modulator. An altered property of the target cell exposed to the modulator is indicative of a modulating effect of the compound.

These and other aspects of the invention as well as various advantages in the utilities will be more apparent with reference to the detailed description of the invention when taken in connection with the accompanying drawings. It is to be understood that the drawings are designed for the purpose of illustration only and are not intended as a definition of the limits of the invention.

Column legends are: "Rabbit medulla mRNA": urea uptake by mRNA-injected oocytes;

"Single clone (UT2)": cRNA-injected oocytes;

CholCl=choline chloride, NaAc=sodium acetate;

"Rabbit medulla RNA": hybrid depletion of poly(A)+ RNA using antisense oligonucleotides corresponding to the 5' end coding region of UT2;

"UT2": hybrid depletion of urea transporter cRNA.

Figure 5:
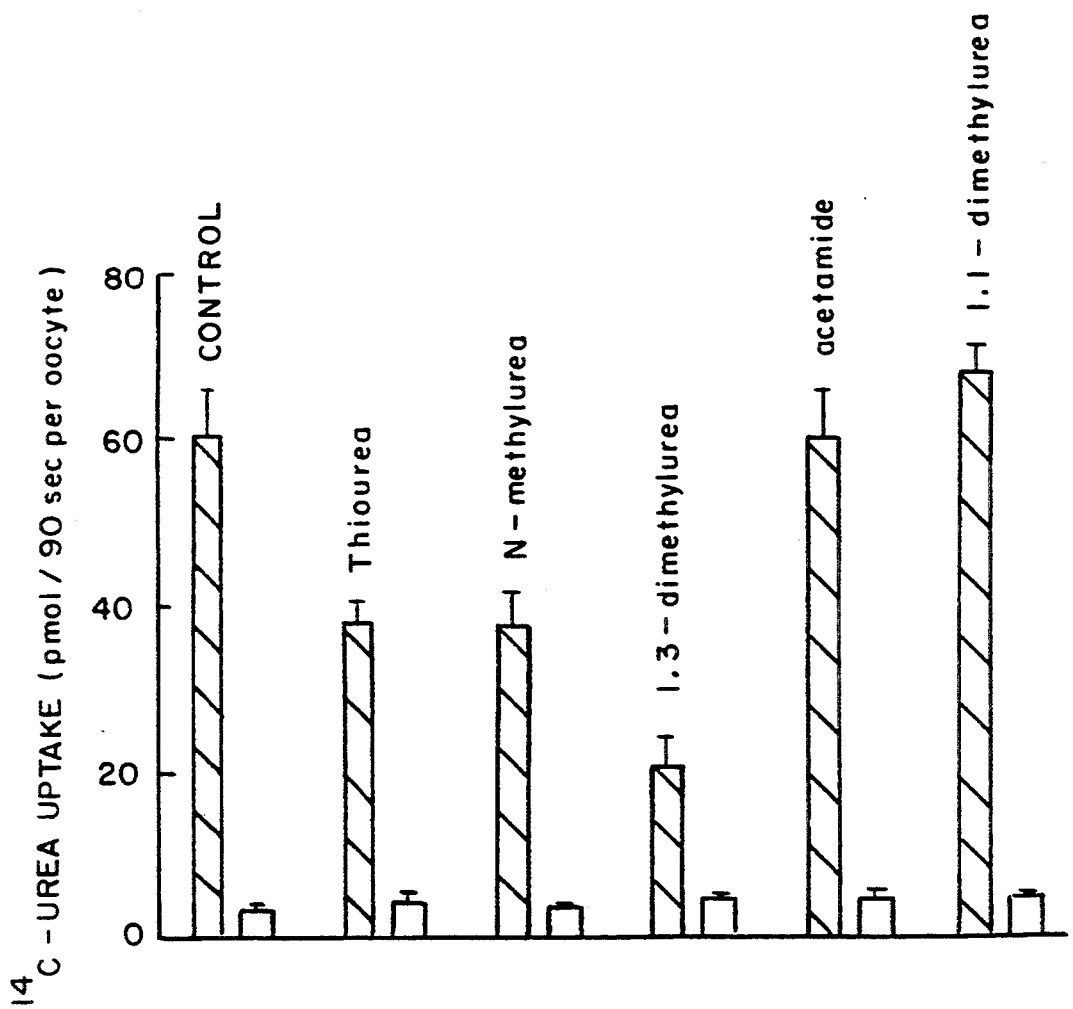

FIG. 5 is a graph illustrating the inhibition of urea uptake by urea analogues. Each column is the mean± s.e.m. (n=6-8 oocytes). Solid columns show uptake into cRNA-injected oocytes. Open columns show uptake in water-injected controls.

Figure 6:
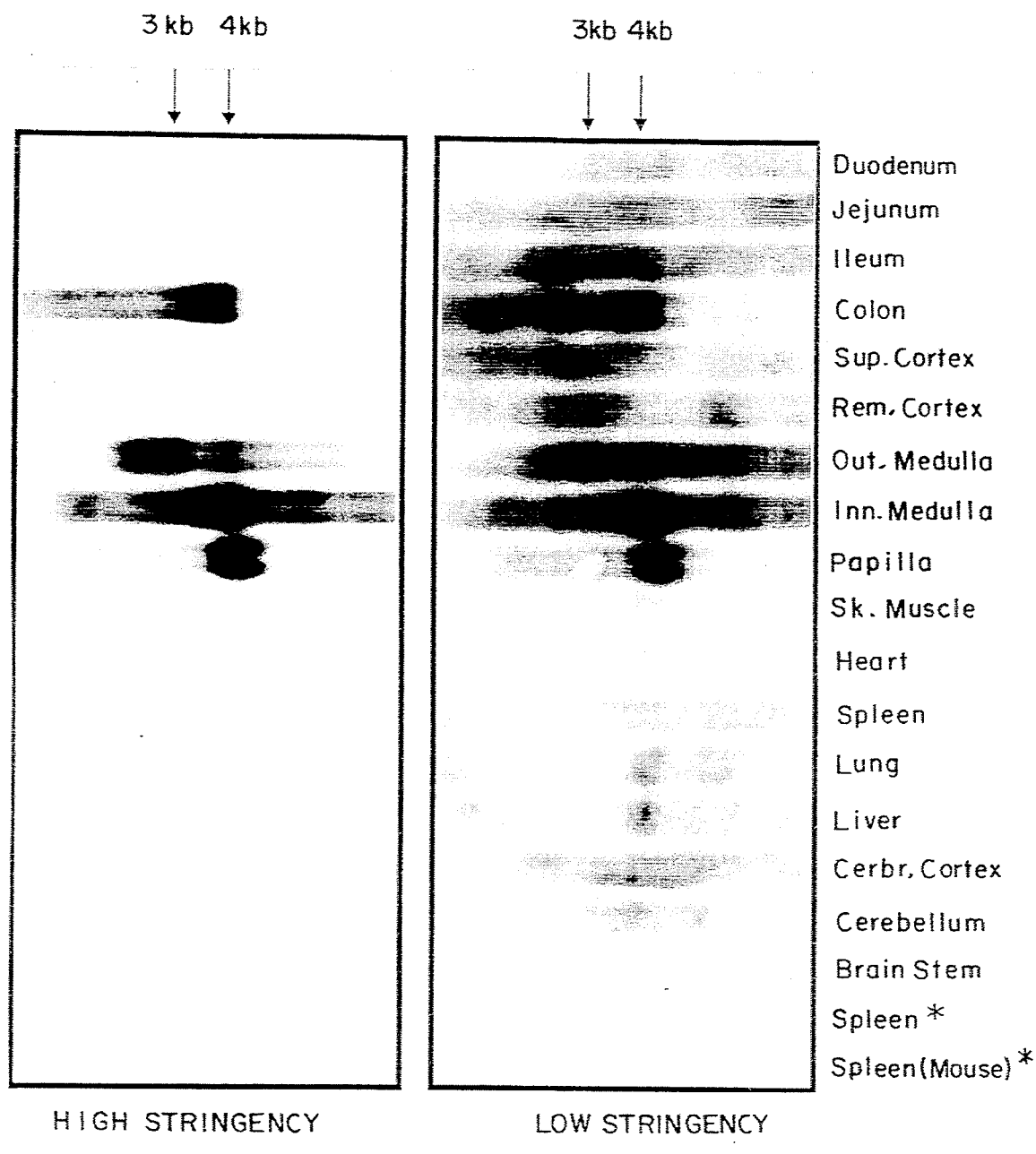

FIG. 6 is a low and high stringency Northern blot analysis of poly (A)+ RNA from rabbit tissues probed with $^{32}$P-labelled urea transporter eDNA. The last two right-hand lanes represent RNA from spleen of anemic (acetyphenyl hydrazine-treated) rabbits or mice. Sup.-=superficial; rem.=remaining; inn.=inner; sk.=skeletal; cebr.=cerebral.

FIG. 7a is a parasagital section of rabbit kidney. Bar=500 m.

FIG. 7b is the outer medulla viewed from a plane tangent to that of FIG. 10a. Bar=200 μm.

FIG. 7c is a cross-sectional view of the IMCD. Bar=100 μm.

Figure 7D:

FIG. 7d is a closeup of the papillary region of FIG. 10a. Bar=200 μm. C.-cortex; OM=outer medulla; IM-=inner medulla; P=papilla.

DETAILED DESCRIPTION OF THE INVENTION

Figure 1:
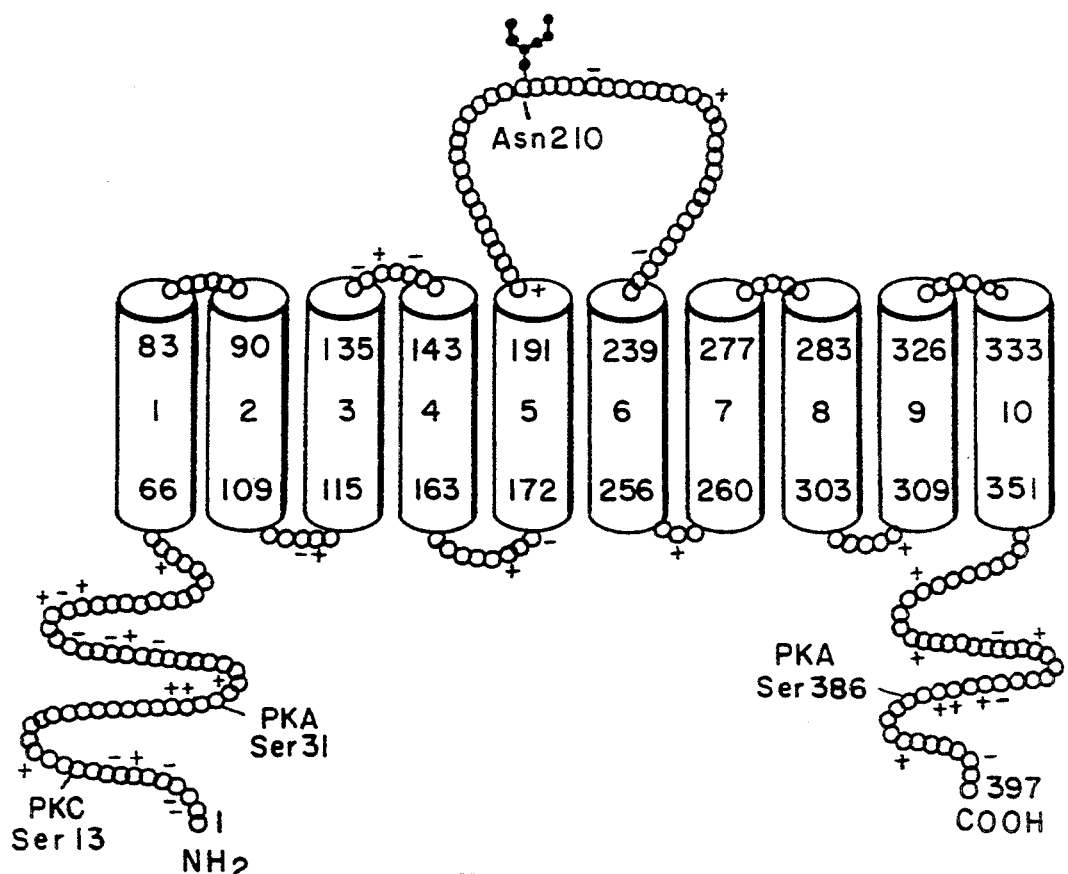
FIG. 1 is a schematic illustration of a membrane model of the urea transporter polypeptide of the invention. Putative membrane spanning regions are depicted as cylinders. Arg, Lys, and His residues are "+" and Glu and Asp are "−". Potential protein kinase PKA and PKC phosphorylation sites are indicated if they are predicted to be cytoplasmic.

The novel molecule of the present invention, hereinafter called, "urea transporter polypeptide" has the schematic structure depicted in FIG. 1, and is a 397-amino acid residue membrane glycoprotein. This glycoprotein mediates urea transport in much the same manner as the vasopressin-sensitive urea transport previously described in vitro in kidney inner medullary collecting ducts (hereinafter "IMCD"). The nucleotide sequence of the urea transporter polypeptide of the invention is not homologous to any known sequence and the polypeptide displays a unique pattern of hydrophobicity. The term "homologous" is necessarily defined relative to a comparsion between two sequences. Given the known pattern of codon degeneracy, any identity between two nucleotide sequences above the codon degeneracy "noise", is considered to be a "signal" of homology. Preferably, at least 50% identity of nucleotide sequence is indicative of a "homologous" sequence.

The urea transporter polypeptide message is found most strongly expressed in IMCD, kidney outer medulla and colon. Related sequences exist in liver and lung. The nucleotide and amino acid sequences, configuration and number of hydrophobic domains, define a unique nucleotide and polypeptide structure.

One embodiment of a urea transporter molecule, according to the invention, is the isolated nucleotide sequence shown in SEQ ID NO.: 1. "Isolated", when applied to the nucleotide sequences encoding the polypeptides of the present invention means an RNA or DNA polymer, portion of genomic nucleic acid, cDNA, or synthetic nucleic acid which, by virtue of its origin or manipulation: (i) is not associated with all of a nucleic acid with which it is associated in nature (e.g., is present in a host cell as a portion of an expression vector); or (ii) is linked to a nucleic acid or other chemical moiety other than that to which it is linked in nature; or (iii) does not occur in nature.

By "isolated" it is further meant a nucleic acid sequence: (i) amplified in vitro by, for example, polymerase chain reaction (PCR); (ii) synthesized by, for example, chemical synthesis; (iii) recombinantly produced by cloning; or (iv) purified, as by cleavage and gel separation.

The term "isolated", when applied to the polypeptides of the present invention means polypeptides: (i) encoded by nucleic acids using recombinant DNA methods; or (ii); synthesized by, for example, chemical synthetic methods; or (iii) separated from naturally-occurring biological materials, and then purified using protein analytical procedures; or (iv) associated with chemical moieties (e.g. polypeptides; carbohydrates, fatty acids, and the like) other than those associated with the polypeptide in its naturally-occurring state; or (v) that do not occur in nature.

SEQ ID NO.: 1 is a 3060 base pair DNA sequence encoding for urea transporter polypeptide that has been isolated from the rabbit kidney medulla. An open reading frame is identified from nucleotides 1025 to 2215 of SEQ ID NO.: 1 and predicts an amino acid sequence of 397 amino acids. The start codon is preceded by multiple stop codons and corresponds to a Kozak initiation of translation site (CCCATGG). The deduced amino acid sequence encoded by this isolated DNA sequence is given in SEQ ID NO. 2. A search of translated sequence databases (NCBI using BLAST TM, Genetics Computer Group, 575 Science Drive, Madison, Wis. 53711, April 1993), reveals that SEQ ID NO.: 2 is not homologous to any known sequence. The search protocol includes amino acid fragments (minimum size about 10 amino acids), so that a plurality of unique fragments can be found within the urea transporter polypeptide of SEQ ID NO.: 2.

A hydropathy analysis of the urea transporter polypeptide (Kyte, J. and R. Doolittle, J. Molec. Biol., 157: 105-132, 1982) of SEQ ID NO.: 2 was performed using a window of 21 amino acids. Briefly, a hydropathy analysis progressively evaluates the hydrophilic and hydrophobic properties of a protein as a scan along its amino acid sequence. There is a singular correspondence between interior portions of soluble, globular proteins and hydrophobicity, and a correspondence between exterior portions and hydrophilicity.

Figure 2:
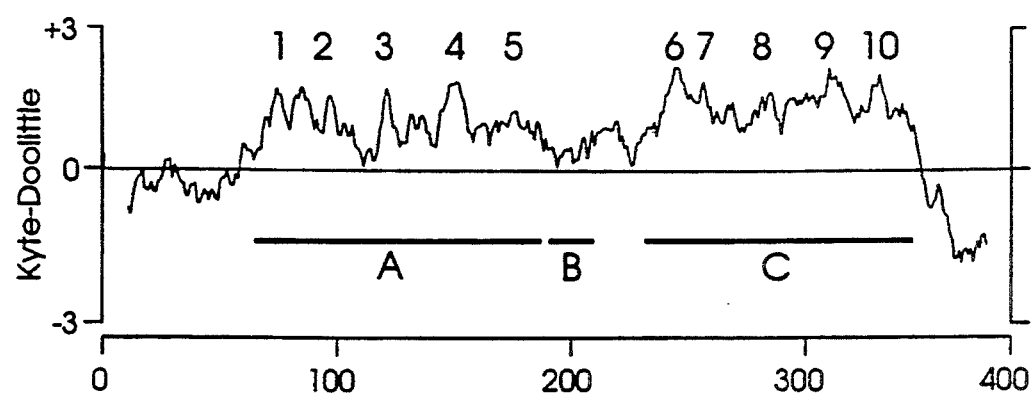
FIG. 2 is a Kyte-Doolittle hydropathy plot using a 21 amino acid residue window. Potential membrane spanning regions are numbered 1–10. A and C denote extended hydrophobic regions.

The hydropathy analysis (FIG. 2) reveals an unusual pattern of hydrophobicity that is different from that of previously studied transporters such as the facilitated glucose transporter GLUT1 (Meuckler, M. et al., Science, 229: 941-945, 1985) and the Na+/glucose co-transporter SGLT1 (Hediger M. et al., Nature 330: 371-381, 1987). These glucose transporters have several spatially distinct hydrophobic transmembrane segments that are interspersed with hydrophilic regions. This pattern is in complete contrast to that of the present urea transporter polypeptide which has extended hydrophobic domains, these domains lacking any interspersed hydrophilic domains (FIG. 2: domains A and C: residues 68–191 and 238–351, respectively). The term "extended" refers to at least two, continuous hydrophobic domains that are at least 75 amino acid residues long, preferably more than about 100 residues long. Potential membrane spanning (hydrophobic) regions 18–21 amino acids long are numbered 1–10. They consist of the numbered "barrels" of FIG. 1; i.e., region 1 extends between amino acid residues 66–83; region 2 extends from residues 90–109, and so on. The letter B denotes a more hydrophilic region and is predicted to be extracellular. The terms "hydrophilic and hydrophobic" in this context are primarily a function of the size of the amino acid "window" used in the hydropathy analysis. For the present purposes, "hydrophilic" refers to a stretch of amino acid sequences at least 21 residues long and scoring less than 0.6 on a Kyte-Doolittle plot; the scores are derived using a window of preferably at least 21 amino acids.

Figure 3:
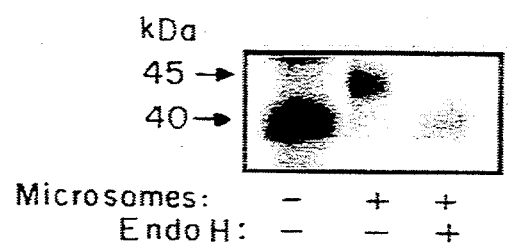
FIG. 3 is an SDS-PAGE blot showing urea transporter polypeptide expression in the absence of pancreatic microsomes (left lane) and the presence of microsomes after centrifugation (middle lane). The right lane shows the product after deglycosylation with endoglycosidase-H.

In vitro translation of urea transporter cRNA was performed using rabbit reticulocyte lysates followed by SDS-PAGE (Example 1; FIG. 3). Results are in agreement with the expected mobility of an integral membrane protein of 397 residues at 40 kDa. Urea transporter polypeptide has two potential N-glycosylation sites (N-X-T/S); namely Asn 210 and Asn 288 (SEQ. ID. NO.: 2). Of these, Asn 288 resides in hydrophobic domain C (membrane region 7 in FIGS. 1 and 2) and is therefore less likely to be glycosylated than Asn 210 which is part of the more hydrophilic domain B.

In the presence of dog pancreatic microsomes, in vitro translation of urea transporter cRNA gave a band corresponding to 45 kDa (Example 1; FIG. 3). This increase in molecular weight was completely reversed by treatment with endoglycosidase-H. A 5–6 kDa shift in molecular weight is indicative of N-glycosylation at a single site. See Hediger, M. et al., Biochem. Biophys. Acta, 1064: 360–364 (1991). Thus, the Asn 210 of urea transporter polypeptide is likely to be glycosylated. The results of the in vitro translation experiments also indicate that there is no large cleavable signal sequence (Example 1; FIG. 3). The urea transporter polypeptide of the present invention has three potential phosphorylation sites: two PKA sites (Ser 31 and Ser 386) and a PKC site (Ser 13—FIG. 1).

These findings suggest that the hydrophilic domain in the center of the urea transporter polypeptide (domain B) is extracellular and the N-terminus is cytoplasmic. This information, in conjunction with the algorithm of Eisenberg et al., (J. Molec. Biol., 179: 125–142, 1984), yields the model shown in FIG. 1. It is, however, conceivable that due to the lack of interspersed hydrophilic domains and the resulting presence of only a few charged residues in domains A and C (FIG. 1) a major portion of the protein is embedded entirely in the membrane making it difficult to resolve individual membrane spanning regions in domains A and C.

Using the nucleotide sequence information provide in SEQ ID NO. 1, cell lines expressing the polypeptide can be established (Example 6). Likewise, homologues to SEQ ID NO.: 1 of other vertebrate (i.e., mammalian) species can be identified using conventional techniques, described in greater detail below. Such genetic engineering techniques are well within the scope of those of ordinary skill in the art.

Northern blot analyses was employed to study the tissue distribution of urea transporter polypeptide in rabbit (see Example 4). Prominent bands of size 4 kb at high stringency were observed in lanes corresponding to renal papillary tip, renal inner medulla and colon (FIG. 6). Within the kidney, the 4 kb signal was strongest in the papillary tip, consistent with the predicted distribution of the vasopressin-regulated urea transporter polypeptide. See, for example, Knepper, M.A., et al., Am. J. Physiol., 256:F610–F621 (1987). The presence of two bands of about 3 kb for the renal outer medulla may either represent the products of the use of different polyadenylation signals or alternately spliced versions of the urea transporter polypeptide gene.

Urea formed in the liver may be disposed of not only by excretion in the urine but also by secretion into the colon where it is hydrolyzed by gut microflora. Ammonia formed in this way may be salvaged and transported to the liver via the portal vein, where it is made available for further metabolic interaction.

Under low stringency conditions, a urea transporter polypeptide probe hybridized to distinct 4 kb bands in liver and lung (FIG. 6, Example 5). A urea transporter in liver would be needed to facilitate exit of synthesized urea from hepaticytes. In vivo studies have failed to reveal saturable urea transport in the lung. See, Effros, R.M., et al., Am. J. Physiol., 263:L619–L626 (1992). The present finding, however, suggests that a urea transporter polypeptide is present in lung tissue.

The urea transporter polypeptide of the present invention is inhibitable by phloretin. See below and Example 4. The expression of a phloretin-inhibitable urea transporter polypeptide message in kidney outer medulla, colon, liver, and lung is a novel finding and further defines the unique structural and functional properties of the present invention. More precise determination of the cellular localization of urea transporter message was studied using in situ hybridization of fixed tissue sections and radiolabelled urea transporter polypeptide antisense cRNA (see FIG. 7, Example 5). Epithelial cells lining the IMCD were stained and a signal in the outer medulla was detected, consistent with Northern blot analysis. The exact tubular location of the outer medulla signal and its functional role are not presently known.

In red blood cells, phloretin-sensitive urea transporters are known to control water efflux during the passage of the blood cells through regions of 0.5–0.6M urea in the kidney. See Brahm, J., J. Gem Physiol., 82:1–23 (1983). On Northern blots, a signal in RNA from spleen of anemic rabbits, which are supposed to contain the message for the red blood cell urea transporter polypeptide, could not be detected (See FIG. 6). This suggests that the red blood cell urea transporter is significantly different from the presently described urea transporter polypeptide.

The saturation kinetics displayed by known urea transporters are generally known to be complex and affinities for urea ($K_m$) have been reported to be greater than 200 mM. The present urea transporter polypeptide expressed in oocytes does not demonstrate saturation of transport using urea concentrations in the concentration range between about 1 and 200 mM urea (Example 4).

A nucleotide sequence encoding urea transporter polypeptide has been cloned, isolated and expressed. A general protocol is present below. This protocol is intended to obtain a cDNA having a complete reading frame for the polypeptide.

A. Cloning Urea Transporter Polypeptide

A cDNA encoding urea transporter polypeptide was cloned by first expressing a urea transporter polypeptide in amphibian oocytes and then identifying the size of the messenger RNA encoding the urea transporter protein (see Example 1). Briefly, total RNA is isolated from whole cells suspected of expressing the urea transporter polypeptide. Poly(A)+ RNA is selected from the total RNA and fractionated using gel electrophoresis. Individual fractions of the mRNA are then purified and these individual fractions are injected into oocytes for in vivo translation. The activity of these individual mRNA fractions is tested in the oocyte assay by measuring, for example, uptake of labelled urea by the oocytes. In addition, in vitro translation of the individual mRNA fractions can be performed using microsomes to estimate the size of the protein translated from the mRNA.

Next, a particular mRNA size of interest is used to prepare a cDNA library using an in vitro expression vector system. Once ligated into the expression vector, synthetic mRNA is prepared from the clones by extracting plasmid cDNA and transcribing this cDNA to a complementary message (cRNA) using standard techniques. The message encoding for urea transporter polypeptide is then purified and injected into oocytes for further functional assays, as described in more detail below.

For sequencing, plasmid cDNA from the clones is extracted and purified by, for example, electrophoresis. The DNA is then cloned into a vector for DNA sequencing, using standard methods, for example, Sambrook, J. et al., Molecular Cloning, Cold spring Harbor Press, N.Y. See, also, Example 1.

B. Cloning a Human Homologue of Urea Transporter Polypeptide

One approach used to screen a DNA library for the presence of a urea transporter nucleotide coding sequence corresponding to a human homologue includes generating preferred probes using the polymerase chain reaction. The probes are produced by using, for example, a human kidney, liver, lung, colon, or cerebellum cDNA library as a template for PCR primers. Based on the degree of codon degeneracy of the predicted amino acid sequence, primers are derived from the rabbit urea transporter nucleotide sequence of SEQ ID NO.: 1.

The product of the PCR reaction is cloned and the human kidney cDNA library rescreened using the PCR product as the probe(s). This preferred method, however, requires identifying human tissue that expresses urea transporter polypeptide as a source of RNA (e.g., human kidney tissue). See Example 2.

Other tissues expressing the human homologue can, however, be identified by RNA analysis, i.e., Northern blot analysis under low stringency conditions. Confirmation of a human tissue as an RNA source and identification of additional sources of tissue can be accomplished by preparing RNA from the selected tissue and performing Northern blot analysis under low stringency conditions using PCR product as the probe(s). A suitable range of such stringency conditions is described in Krause, M.H., and Aaronson, S.A., 1991, Methods in Enzymology 200: 546–556. Additionally, genomic libraries can be screened for the presence of the human homolog coding sequence using a PCR generated probe(s).

C. Testing and Cloning Related Urea Transporter Molecules

The invention also pertains to a more general protocol for isolating the gene for the urea transporter polypeptide from vertebrates, in particular from non-human vertebrates such as cows, pigs, monkeys and the like. In this approach, total mRNA can be isolated from mammalian tissues or from cell lines likely to express urea transporter polypeptide. In general, total RNA from the selected tissue or cell culture is isolated using conventional methods. Subsequent isolation of mRNA is typically accomplished by oligo (dT) chromatography. Messenger RNA for Northern analysis is size-fractionated by electrophoresis and the RNA transcripts are transferred to nitrocellulose according to conventional protocols (Sambrook, J. et al., Molecular Cloning, Cold spring Harbor Press, N.Y.).

A labelled PCR-generated probe capable of hybridizing with the rabbit urea transporter nucleotide (SEQ ID NO.: 1) can serve to identify RNA transcripts complementary to at least a portion of the rabbit urea transporter gene. For example, if Northern analysis indicates that RNA isolated from a cow kidney hybridizes with the labelled probe, then a cow kidney cDNA library is a likely candidate for screening and identification of a clone containing the coding sequence for a cow homolog of urea transporter polypeptide.

Northern analysis is used to confirm the presence of mRNA fragments which hybridize to a probe corresponding to all or part of the urea transporter polypeptide. Northern analysis indicates the presence and size of the transcript. This allows one to determine whether a given cDNA clone is long enough to encompass the entire transcript or whether it is necessary to obtain further cDNA clones, i.e., if the length of the cDNA clone is less than the length of RNA transcripts as seen by Northern analysis. If the cDNA is not long enough, it is necessary to perform several steps such as: (i) rescreen the same library with the longest probes available to identify a longer cDNA; (ii) screen a different cDNA library with the longest probe; and (iii) prepare a primer-extended cDNA library using a specific nucleotide primer corresponding to a region close to, but not at, the most 5' available region. This nucleotide sequence is used to prime reverse transcription. The primer extended library is then screened with the probe corresponding to available sequences located at 5' to the primer. See for example, Rupp et al., Neuron, 6:811–823 (1991).

The preferred clone of urea transporter polypeptide has a complete coding sequence, i.e., one that begins with methionine, ends with a stop codon, and preferably has another in-frame stop codon 5' to the first methionine. It is also desirable to have a cDNA that is "full length", i.e. includes all of the 5' and 3' untranslated sequences. To assemble a long clone from short fragments, the full-length sequence is determined by aligning the fragments based upon overlapping sequences. Thereafter, the full-length clone is prepared by ligating the fragments together using the appropriate restriction enzymes.

As discussed above, PCR-generated probes can be used in the protocol for isolating mammalian homologues to urea transporter polypeptide. Moreover, probes to be used in the general method for isolating vertebrate urea transporter polypeptide can now include oligonucleotides, all of which encode part of the rabbit sequence shown in SEQ ID NO.: 1. Unlike the PCR approach to generating a probe, the above-identified probes do not require prior isolation of RNA from a tissue expressing the vertebrate homolog.

In particular, an oligodeoxynucleotide probe typically has a sequence somewhat longer than that used for the PCR primers. A longer sequence is preferable for the probe, and it is important that codon degeneracy be minimized. A representative protocol for the preparation of an oligonucleotide probe for screening a cDNA library is described in Sambrook, J. et al., Molecular Cloning, Cold Spring Harbor Press, New York, 1989. In general, the probe is labelled, e.g., $^{32}$p, and used to screen clones of a cDNA or genomic library.

Alternately, an expression library can be screened using conventional immunization techniques, such as those described in Harlowe and Lane, D. (1988), Antibodies, Cold Spring Harbor Press, New York. Antibodies prepared using purified urea transporter polypeptide as an immunogen are preferably first tested for cross reactivity with the homolog of urea transporter polypeptide from other species. Other approaches to preparing antibodies for use in screening DNA libraries, as well as for use in diagnostic and research applications, are described below. See Example 3.

D. Nucleic Acid and Protein Sequences

The nucleic acid sequence of the rabbit urea transporter polypeptide is depicted in SEQ ID NO.: 1. This sequence, its functional equivalent, or unique fragments of this sequence may be used in accordance with the invention. The term "unique fragments" refers to portions of the urea transporter nucleic acid sequence that find no counterpart in the known sequences of other polypeptides. Subsequences comprising hybridizable portions of the urea transporter sequence have use, e.g., in nucleic acid hybridization assays, Southern and Northern blot analyses, etc.

Nevertheless, the nucleic acid sequence depicted in SEQ ID NO: 1 can be altered by mutations such a substitutions, additions or deletions that provide for functionally equivalent nucleic acid sequences. According to the present invention, a nucleic acid sequence is "functionally equivalent" compared with the nucleic acid sequence depicted in SEQ ID NO.: 1, if it satisfies at least one of the following conditions: (i) the nucleic acid sequence has the ability to hybridize to a urea transporter nucleotide sequence, but it does not necessarily hybridize to that sequence with an affinity that is the same as that of the naturally occurring urea transporter nucleic acid sequence; and/or (ii) the nucleic acid can serve as a probe to distinguish between the present urea transporter sequences and other nucleotide sequences.

The term "probe", therefore, refers to a ligand of known qualities that can bind selectively to a target. As applied to the nucleic acid sequences of the invention, the term "probe" refers to a strand of nucleic acid having a base sequence complementary to a target sequence. Preferred nucleotide sequences may hybridize if they contain sequences that have at least 50% identity to a target sequence. A preferred probe that can distinguish between a urea transporter sequence and other sequences refers to a probe that includes SEQ ID NO.: 1, functional variants, or unique fragments thereof.

Because the nucleic acid sequence of urea transporter polypeptide is now known, those of ordinary skill in the art can readily determine nucleic acid sequences of the urea transporter polypeptide that are not homologous to any other nucleic acid sequence, including other urea transporter sequences. These non-homologous sequences, and peptides encoded by them, are referred to as "unique" fragments and are meant to be included within the scope of the present invention.

Moreover, due to the degeneracy of nucleotide coding sequences, other nucleic acid sequences may be used in the practice of the present invention. These include, but are not limited to, sequences comprising all or portions of the urea transporter sequences depicted in SEQ ID NO.: 1 which are altered by the substitution of different codons that encode the same amino acid residue within the sequence, thus producing a silent change. Such altered sequences are regarded as equivalents of the specifically claimed sequences.

Urea transporter polypeptides or unique fragments or derivatives thereof include, but are not limited to, those containing as a primary amino acid sequence all, or unique parts of the amino acid residues substantially as depicted in SEQ ID NO.: 2, including altered sequences in which functionally equivalent amino acid residues are substituted for residues within the sequence, resulting in a silent change. According to the invention, an amino acid is "functionally equivalent" compared with the sequences depicted in SEQ ID NO.: 2 if the amino acid sequence contains one or more amino acid residues within the sequence which can be substituted by another amino acid of a similar polarity which acts as a functional equivalent. Substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Substantial changes in functional or, for example, immunological properties may be made by selecting substitutes that differ from the original amino acid residue. More significantly, the substitutions are chosen for their effect on: (i) maintaining the structure of the peptide backbone in the area of the substitution, for example, as a sheet or helical conformation; (ii) maintaining the charge or hydrophobicity of the molecule at the target side; or (iii) maintaining the bulk of the side chain. The substitutions that in general are expected to induce greater changes are those in which: (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

Most deletions and insertions in the urea transporter polypeptide, and substitutions in particular, are not expected to produce radical changes in the characteristics of the polypeptide. Nevertheless, when it is difficult to predict the exact effect of the substitution, deletion, or insertion in advance of doing so, one skilled in the art will appreciate that the effect will be evaluated using routine screening assays as described below. For example, a change in the immunological character of the urea transporter polypeptide, such as binding to a given antibody, is measured by an immunoassay such as a competitive type immunoassay.

Also included within the scope of the invention are urea transporter polypeptides or unique fragments or derivatives thereof which are differentially modified during or after translation, e.g., by phosphorylation, glycosylation, crosslinking, acylation, proteolytic cleavage, linkage to an antibody molecule, membrane molecule or other ligand, (Ferguson, et al., 1988, Ann. Rev. Biochem. 57:285–320).

In addition, the recombinant urea transporter polypeptide-encoding nucleic acid sequences of the invention may be engineered so as to modify processing or expression of the urea transporter protein. For example, and not by way of limitation, the urea transporter nucleotide sequence(s) may be combined with a promoter sequence and/or a ribosome binding site using well characterized methods, and thereby facilitate harvesting or bioavailability.

Additionally, a given urea transporter nucleotide sequence can be mutated in vitro or in vivo, to create variations in coding regions and/or form new restriction endonuclease sites or destroy preexisting ones, to facilitate further in vitro modification. Any technique for mutagenesis known in the art can be used including, but not limited to, in vitro site-directed mutagenesis (Hutchinson, et al., 1978, J. Biol. Chem. 253:6551), use of TAB ® linkers (Pharmacia), PCR-directed mutagenesis, and the like.

In addition to generating fragments of urea transporter polypeptide from expression of cloned partial sequences of urea transporter DNA, fragments of urea transporter polypeptides can be generated directly from the intact polypeptide. Proteins are specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the $\epsilon$-amino groups of lysine with ethyltrifluorothioacetate in mildly basic solution yields a blocked amino acid residue whose adjacent peptide bond is no longer susceptible to hydrolysis by trypsin. Goldberger et al. Biochem., 1: 401 (1962). Treatment of such a polypeptide with trypsin thus cleaves only at the arginyl residues.

Polypeptides also can be modified to create peptide linkages that are susceptible to proteolytic enzyme catalyzed hydrolysis. For example, alkylation of cysteine residues with $\beta$-halo ethylamines yields peptide linkages that are hydrolyzed by trypsin. Lindley, *Nature*, 178:647 (1956). In addition, chemical reagents that cleave polypeptide chains at specific residues can be used. Withcop, *Adv. Protein Chem.* 16:221 (1961). For example, cyanogen bromide cleaves polypeptides at methionine residues. Gross & Witkip, J. Am Chem Soc., 83: 1510 (1961). Thus, by treating urea transporter polypeptide or fragments thereof with various combinations of modifiers, proteolytic enzymes and/or chemical reagents, numerous discrete overlapping peptides of varying sizes are generated. These peptide fragments can be isolated and purified from such digests by chromatographic methods.

Alternatively, urea transporter polypeptides can be synthesized using an appropriate solid state synthetic procedure. Steward and Young, *Solid Phase Peptide Synthesis*, Freemantle, San Francisco, Calif. (1968). A preferred method is the Merrifield process. Merrifield, *Recent Progress in Hormone Res.*, 23:451 (1967). The activity of these peptide fragments may conveniently be tested using, for example, an oocyte expression assay as described herein.

The urea transporter sequences of the invention also include non-rabbit homologues of the amino acid sequence of SEQ ID NO.: 2. The urea transporter polypeptides of the invention may be prepared by recombinant nucleic acid expression techniques or by chemical synthesis using standard peptide synthesis techniques.

Also within the scope of the invention are nucleic acid sequences or proteins encoded by nucleic acid sequences derived from the same gene but lacking one or more structural features as a result of alternative splicing of transcripts from a gene that also encodes the complete urea transporter gene, as defined previously.

Nucleic acid sequences complementary to DNA or RNA sequences encoding urea transporter polypeptide or a functionally active portion(s) thereof are also provided. In animals, particularly transgenic animals, RNA transcripts of a desired gene or genes may be translated into polypeptide products having a host of phenotypic actions. In a particular aspect of the invention, antisense oligonucleotides can be synthesized. These oligonucleotides may have activity in their own right, such as antisense reagents which block translation or inhibit RNA function. Thus, where urea transporter polypeptide is to be produced utilizing the nucleotide sequences of this invention, the DNA sequence can be in an inverted orientation which gives rise to a negative sense ("antisense") RNA on transcription. This antisense RNA is not capable of being translated to the desired urea transporter product, as it is in the wrong orientation and would give a nonsensical product if translated.

Expression of Urea Transporter Polypeptide

The present invention also permits the expression, isolation, and purification of the urea transporter polypeptide. A urea transporter nucleotide sequence may be cloned or subcloned using any method known in the art. Because some post-translational events such as glycosylation, phosphorylation, and/or subunit assembly may not be carded out in the same manner in amphibian oocytes as in mammalian cells, the preferred expression systems utilize mammalian cells and cell lines. A large number of vector-mammalian host systems known in the art may be used. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript ® (Stratagene) plasmid derivatives. Recombinant urea transporter molecules can be introduced into host cells via transformation, transfection, infection, electroporation, etc. Generally introduction of urea transporter molecules into a host is accomplished using a vector containing urea transporter DNA under control by regulatory regions of the DNA that function in the host cell.

In one method of expressing urea transporter polypeptide, the cDNA that corresponds to the entire coding region ( SEQ ID NO.: 1 ) is moved by way of a eukaryotic expression vector into cells derived from the simian kidney (e.g., COS-7 cells). Expression is monitored after transfection with lipofectin by measuring the initial rate of radiolabelled urea uptake. See Example 6.

The details of this experimental approach for transfection, selection and characterization of the urea transporter polypeptide are similar to those that have been used previously (see, for example, Birnir, B. et al., Biochem. Biophys. Acta, 1048:100–104 (1990), the entire contents of which are incorporated herein by reference.

Once the polypeptide is expressed, it may be isolated and purified by standard methods including chromatography (e.g., ion exchange, affinity, and sizing column chromatography), centrifugation, differential solubility, or by any other standard technique for the purification of proteins. In particular, urea transporter polypeptide be isolated by binding to an affinity column comprising antibodies to urea transporter polypeptide bound to a stationary support.

F. Preparation of Antibodies to Urea Transporter Polypeptide

The term "antibodies" is meant to include monoclonal antibodies, polyclonal antibodies and antibodies prepared by recombinant nucleic acid techniques that are selectively reactive with urea transporter polypeptide. The term "selectively reactive" refers to those antibodies that react with one or more antigenic determinants of urea transporter polypeptide, and do not react with other transporter polypeptides. Determinants usually consist of chemically active surface groupings of molecules such as amino acids or sugar side chains and have specific three dimensional structural characteristics as well as specific charge characteristics. Antibodies include antibodies raised against rabbit polypeptide (SEQ ID NO.: 2) and intended to cross-react with a human homolog. These antibodies are useful for diagnostic applications. Other antibodies include antibodies raised against rabbit urea transporter polypeptide, which antibodies are generally used for research purposes. These antibodies include those raised against short, synthetic peptides of the rabbit sequence.

Finally, antibodies may be raised against a human homolog and isolated by standard protein purification methods. Generally, a peptide immunogen is first attached to a carrier to enhance the immunogenic response. Although the peptide immunogen can correspond to any portion of the amino acid sequence of the human urea transporter protein or to variants of the sequence, such as the amino acid sequences corresponding to the primers and probes described, certain peptides are more likely than others to provoke an immediate response. For example, a peptide including the C-terminal amino acid is more likely to generate an antibody response.

Other alternatives to preparing antibodies reactive with the human homolog include: immunizing an animal with a protein expressed by a procaryotic (e.g., bacterial) or eucaryotic cell, which cell includes the coding sequence for: (i) all or part of the human homolog; or (ii) the coding sequence for all or part of the rabbit urea transporter polypeptide. Antibodies can also be prepared by immunizing an animal with whole cells that are expressing all or a part of a cDNA encoding the urea transporter protein. For example, cDNA encoding the urea transporter polypeptide of the present invention may be expressed in a host using standard techniques (see Sambrook et al., Molecular Cloning; A Laboratory Manual, Cold Spring Harbor Press, Cole Spring Harbor, N.Y. (1989) such that 5–20% of the total of protein recovered is urea transporter polypeptides. Proteins are electrophoresed using PAGE, the appropriate band cut, the protein eluted, and prepared for immunization. Mice are immunized twice intraperitoneally with 50 micrograms protein immunogen per mouse. Their sera is tested for antibody activity by immunohistology or immunocytology on any urea transporter polypeptide expressing cell system (e.g., transfected oocytes) and by F-LISA with the expressed urea transporter polypeptide. For immunohistology, a biotin-conjugated anti-mouse immunoglobulin is used followed by avidin-peroxidase, and a chromogenic peroxidase substrate. Such preparations are commercially available; for example, from Zymad Corp., San Francisco, California. Animals with serum antibodies are sacrificed three days later and their spleens taken for fusion and hybridoma production, as above. Positive supernatants are tested as above and by, for example, Western blot analysis.

To further improve the likelihood of producing an anti-urea transporter immune response, the amino acid sequence of the urea transporter polypeptide may be analyzed in order to identify portions of the molecule which may be associated with increased immunogenicity. For example, the amino acid sequence may be subjected to computer analysis to identify surface epitopes which present computer-generated plots of antigenic index, an amphophilic helix, amphophilic sheet, hydrophilicity, and the like. Alternatively, the deduced amino acid sequences of urea transporter polypeptide from different species could be compared, and relatively nonhomologous regions identified. These non-homologous regions would be more likely to be immunogenic across various species.

For preparation of monoclonal antibodies directed toward urea transporter polypeptide, any technique which provides for the production of antibody molecules by continuous cell lines and culture may be used. For example, the hybridoma technique originally developed by Kohler and Milstein (Nature, 256: 495–497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to form anti-urea transporter antibodies (Ladner et al. U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to anti-urea transporter monoclonal antibodies or other molecules of the invention. See, for example, "Conjugate Vaccines", Contributions to Microbiology and Immunology, J.M. Cruse and R.E. Lewis, Jr (eds), Carger Press, New York, (1989), the entire contents of which are incorporated herein by reference.

Coupling may be accomplished by any chemical reaction that will bind the two molecules so long as the antibody and the other moiety retains their respective activities. This linkage can include many chemical mechanisms, for instance covalent binding, affinity binding, intercalation, coordinate binding and complexation. The preferred binding is, however, covalent binding. The covalent binding can be achieved either by direct condensation of existing side chains or by the incorporation of external bridging molecules. Many bivalent or polyvalent linking agents are useful in coupling protein molecules, such as an anti-urea transporter monoclonal antibody, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myesthenia Gravis by toxin-acetylcholine receptor conjugates." Jour. Immun. 133:1335-2549; Jansen, F.K., H.E. Blythman, D. Carriere, P. Casella, O. Gros, P. Gros, J.C. Laurent, F. Paolucci, B. Pau, P. Poncelet, G. Richer, H. Vidal, and G.A. Voisin. 1982. "Immunotoxins: Hybrid molecules combining high specificity and potent cytotoxicity". Immunological Reviews 62: 185-216; and Vitetta et al., supra).

Preferred linkers are described in the literature. See, for example, Ramakrishnan, S. et al., Cancer Res. 44:201-208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. #21558G); (iii)SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In other embodiments, compositions of the invention can be used as reagents in immunoassays to detect antibodies against urea transporter polypeptide. Immunoassays can be any of the conventional assay types. For example, a sandwich assay can be performed in which the urea transporter polypeptide of the invention is affixed to a solid phase. A liquid sample such as kidney or intestinal fluid containing, or suspected of containing, antibodies directed against urea transporter polypeptide is incubated with the solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid phase and the label bound to the solid phase is measured, the amount of the label detected serving as a measure of the amount of anti-urea transporter antibody present in the sample. These and other immunoassays can be easily performed by those of ordinary skill in the art using the present compositions as reagents. Such fragments are typically produced by proteolytic cleavage using enzymes such a papain or pepsin, using methods well known in the art.

Radioactive isotopes can be detected by such means as the use of a gamma counter or assimilation counter or by autoradiography. For example, reference by Work, T.S. et al., laboratory techniques and biochemistry and molecular biology, North Holland Publishing Company, New York 1978.

G. Assays/Utilities

The present invention provides for assay systems in which activity or activities resulting from exposure to a peptide or non-peptide compound may be detected by measuring a physiological response to the compound in a cell or cell line which expresses the molecules of the invention. A "physiological response" may comprise any biological response, including but not limited to transcriptional activation of certain nucleic acid sequences (e.g.. promoter/enhancer elements as well as structural genes), translation, or phosphorylation, the induction of urea transport across a cell membrane, activation by recruitment of transporter molecules from intracellular vesicles in response to vasopressin, increases in cyclic AMP levels, and morphological changes, such as changes in oocyte volume.

The present invention thus provides for the development of novel assay systems which may be utilized in the screening of compounds directed against urea transporter polypeptide. Target cells expressing urea transporter polypeptide, which are modulated (i.e., activated and/or inhibited) by the compounds, may be produced by transfection with urea transporter polypeptide-encoding nucleic acid.

A convenient assay method for identifying a modulator of a urea transport polypeptide includes providing a urea transporter messenger RNA to a target cell such as an amphibian oocyte; incubating the oocyte in the presence of the modulating compound; and measuring the uptake of, for example, radiolabelled urea into the oocytes. Alternately, one could measure expression of the messenger RNA into the urea transporter polypeptide. In particular, using radiolabelled uptake, or measurement of physical changes in the oocyte such as, for example, changes in volume, one can rapidly screen many compounds of interest in a short period of time.

An exemplary assay method for identifying a modulator of a urea transport polypeptide may include providing a target cell containing an isolated nucleotide sequence which encodes for a urea transporter polypeptide; maintaining the target cell under conditions and for a time sufficient for the urea transporter polypeptide to be expressed in the target cell; exposing the target cell to a compound suspected of modulating urea transporter polypeptide activity; measuring a property of the target cell in the presence of the modulator; and comparing this property to that of a target cell in the absence of the modulator but containing the isolated nucleotide sequence. An altered property of the target cell exposed to the modulator is indicative of a modulating effect of the compound.

Moreover, assay systems can be based on mammalian cell lines in which the urea transporter nucleotide sequence of interest is transfected into the cell lines and the cell lines subsequently screened for modulators of urea transport. Transfection of mammalian cell lines with eukaryotic DNA is well known and the techniques have been described extensively in the literature. See, for example Sambrook, J. et al., Molecular Cloning, Cold Spring Harbor Press, New York, 1989, the entire contents of which are incorporated herein by reference.

Once target cell lines are produced or identified, it may be desirable to select for cells which are exceptionally sensitive to a particular compound. Such target cells may express large amounts of urea transporter polypeptide. Target cells expressing a relative abundance of the polypeptide could be identified by selecting target cells which, when incubated with a compound/tag, produce a relatively higher degree of urea uptake. Alternatively, cell lines which are exceptionally sensitive to a compound may exhibit a relatively strong biological response, such as a sharp increase in immediate early gene products such as c-fos or c-jun, in response to urea transporter polypeptide expression. By developing assay systems using target cells which are extremely sensitive to a compound, the present invention provides for methods of screening for low levels of urea transporter activity.

In particular, using recombinant DNA techniques, the present invention provides for urea transporter target cells which are engineered to be highly sensitive to modulating compounds. For example, the urea transporter gene, cloned according to the methods set forth above, may be inserted into cells which naturally express urea transporter polypeptide such that the recombinant urea transporter gene is expressed at high levels. Since urea transporters induce urea transport, cells expressing a urea transporter polypeptide may find use in urea bioassay methods, particularly in clinical settings where elevated urea may be indicative of kidney dysfunction.

The present invention also provides for experimental model systems for studying the physiological role of the native urea transporter polypeptide. In these model systems, urea transporter polypeptide, peptide fragment, or a derivation thereof, may be either supplied to the system or produced within the system. Such model systems could be used to study the effects of urea transporter excess or depletion. The experimental model systems may be used to study the effects of increased or decreased response to ligand in cell or tissue cultures, in whole animals, or in particular cells or tissues within whole animals or tissue culture systems, or over specified time intervals (including during embryogenesis).

In additional embodiments of the invention, a urea transporter sequence may be used to inactivate the endogenous gene by homologous recombination, and thereby create a urea transporter-deficient cell, tissue, or animal. For example, and not by way of limitation, a recombinant urea transporter nucleotide sequence may be engineered to contain an insertional mutation (e.g., the neogene) which, when inserted, inactivates transcription of urea transporter polypeptide. Such a construct, under the control of a suitable promoter operatively linked to the urea transporter nucleotide sequence, may be introduced into a cell by a technique such as transfection, transduction, injection, etc. In particular, stem cells lacking an intact urea transporter gene may generate transgenic animals deficient in urea transporter polypeptide. In a specific embodiment of the invention (See Example 8), the endogenous urea transporter gene of a cell may be inactivated by homologous recombination with a mutant urea transporter gene to form a transgenic animal lacking the ability to express urea transporter polypeptide. In another embodiment, a construct can be provided that, upon transcription, produces an "anti-sense" nucleic acid sequence which, upon translation, will not produce the required urea transporter polypeptide.

A "transgenic animal" is an animal having cells that contain DNA which has been artificially inserted into a cell, which DNA becomes part of the genome of the animal which develops from that cell. The preferred DNA encodes for urea transporter polypeptide and may be entirely foreign to the transgenic animal or may be homologous to the natural urea transporter polypeptide of the transgenic animal, but which is inserted into the animal's genome at a location which differs from that of the natural homolog.

In a further embodiment of the invention, urea transporter polypeptide expression may be reduced by providing urea transporter- expressing cells, preferably in a transgenic animal, with an amount of urea transporter anti-sense RNA or DNA effective to reduce expression of urea transporter polypeptide.

A transgenic animal (preferably a non-human mammal) can also be provided with a urea transporter DNA sequence that also encodes a repressor protein that can bind to a specific DNA sequence of urea transporter, thereby reducing ("repressing") the level of transcription of urea transporter DNA.

Transgenic animals of the invention which have attenuated levels of urea transporter polypeptide expression have general applicability to the field of transgenic animal generation, as they permit control of the level of expression of genes.

According to the present invention, urea transporter probes may be used to identify cells and tissues of transgenic animals which lack the ability to transcribe urea transporter polypeptide. Urea transporter polypeptide expression may be evidenced by transcription of urea transporter mRNA or production of urea transporter polypeptide, deterred using probes as described above. One variety of probe which may be used to detect urea transporter expression is a nucleic acid probe, containing a sequence encoding for two adjacent hydrophobic domains lacking hydrophilic domains interspersed among the hydrophobic domains. Detection of urea transporter-encoding mRNA may be easily accomplished by any method known in the art, including, but not limited to, in situ hybridization, Northern blot analysis, or PCR related techniques. Another variety of probe which may be used to anti-urea transporter polypeptide antibody.

The above-mentioned probes may be used experimentally to identify cells or tissues which hitherto had not been shown to express urea transporter polypeptide. Furthermore, these methods may be used to identify the expression of urea transporter polypeptide by aberrant tissues, such as malignancies.

Those of ordinary skill in the art will recognize that modulators of urea transporter polypeptide may have potential therapeutic applications. The compositions and assays described herein may provide with the development of strategies for the treatment of patients with disorders of water excretion (including SIADH syndrome of inappropriate antidiuretic hormone secretion) and possibly edema (excessive accumulation of fluid in the interstitial space, for example due to alteration of cardiac function) and heart failure. When volume and blood pressure decrease, the kidneys decrease sodium and water excretion, thereby increasing the volume of extracellular fluid. This helps to restore the volume and the pressure to normal. Drugs which inhibit urea transport in the terminal IMCD will increase water excretion without increasing sodium excretion. Therefore, the development of drugs which selectively inhibit urea transport is expected to provide an important advantage over drugs that inhibit sodium chloride transport, such as loop-diuretics (thiazides, etc.), since inhibition of urea transport allows water to be excreted without concomitant excretion of sodium.

Furthermore, uremia occurs in kidney disease is characterized by reduced extrarenal clearance of urea. The mechanism of this reduction is not known at present. The most likely explanation is that chronic uremia induces a change in gut mucosa that in some way limits the transport of urea. Drugs which stimulate urea transport in the colon would be of great benefit for patients with uremia.

As mentioned above, a major portion of urea produced in the liver is disposed of by secretion into the colon followed by hydrolysis and conversion into ammonia by gut micro flora. The ammonia is returned to the liver through the portal vein where it is incorporated into amino acids and other compounds. Studies have indicated that there is an absolute increase in the urea nitrogen salvaged in the colon when the metabolic demand for nitrogen exceeds that available from the diet. Selective inhibition of urea transport into the colon may help to protect patients who have liver disease from ammonia intoxication. Ammonia intoxication is characterized by tremors, slurred speech, blurred vision, and in severe cases, coma and death.

The invention will be further illustrated by the following, non-limiting examples:

Example 1: Cloning the Urea Transporter Gene

A: Cloning

Total RNA was isolated from kidney medulla of female New Zealand white rabbits by the guanidium thiocyanate/cesium triflouroacetate method. Poly (A)+RNA (i.e., mRNA) was selected by oligo-dT cellulose chromatography (Collaborative Research, Waltham, Mass.) for injection into oocytes, as described below. Messenger RNA was dissolved in water (0.2–1 microgram/microliter).

Poly (A)+ RNA was fractionated according to size by preparative agarose gel electrophoresis using the method of Hediger, Anal. Biochem., 142:445–454 (1984); and 159:280–286 (1986), the entire contents of which are incorporated herein by reference. Preparative gel electrophoresis offers significant advantages in the present method for separating RNA over sucrose density gradient ultracentrifugation or PAGE electrophoresis. Although separations have been made difficult by technical problems, these problems have been overcome by the preparative gel electrophoresis apparatus of Hediger, U.S. Pat. No. 4,479,861. By using preparative gel electrophoresis, mRNA may be separated at considerably higher resolution than conventional RNA fractionation techniques such as ultracentrifugation. The enhanced separation capability of preparative gel electrophoresis allows one to enrich the desired transporter message to a greater degree than with prior RNA separation methods. This substantially reduces the number of clones to be screened, and the likelihood that a functional cDNA clone can be isolated, using expression cloning.

Messenger RNA (300–500 $\mu$g) (about 1 $\mu$g/$\mu$l) was denatured by heating for about 2 minutes at 70° C. and then rapidly cooled on ice. Separation was performed on a nondenaturing 1.5% agarose gel at about 2° C. The gel running buffer was 10 mM sodium phosphate buffer (pH 6.5). Aliquots of the fractions were precipitated with ethanol and analyzed on a 1% agarose minigel containing 2.2M formaldehyde. Individual fractions of the size range of interest were purified using Nesorb 20 cartridges (New England Nuclear Corporation). Messenger RNA was eluted from the cartridges with 20% propanol and then precipitated with ethanol. The pellet was dissolved in water and assayed by in vivo and in vitro translation.

In vitro translation of urea transporter polypeptide using cRNA (0.1 $\mu$g) was carried out with rabbit reticulocyte lysates (Promega Biotec, Madison Wis.) and sulfur-35-labelled methionine (New England Nuclear) in the presence and absence of canine pancreatic microsomes. The translation mixture without microsomes was supplemented with 0.5% triton X-100 to improve solubility of the urea transporter polypeptide. Reaction containing microsomes (20 $\mu$l) were supplemented with 50 $\mu$l buffer (3.5% glycerol, 10 mM tris pH 7.5) and pelleted for 30 minutes at 4° C. in a microcentrifuge. The pellet was suspended in 20 $\mu$l of the above buffer and haft of this is treated with endoglycosidase-H (5 mU) (Boehringer Mannheim) in the final volume of 50 $\mu$l. Translation products were separated on SDS-PAGE using a 15% gel. The dried SDS-gel was treated with enhancer (Autofluor, National Diagnostics), and analyzed by autoradiography. Sodium+/glucose co-transporter cRNA was used in control experiments.

The rabbit kidney medulla mRNA that is size fractionated by the preparative agarose gel electrophoresis was analyzed by oocyte expression assay. Large, fully grown oocytes (stage 5 and 6) with a diameter of 1.2–1.3 mm were hand dissected from ovarian fragments of Xenopus laevis, treated with 2 mg/ml type 1A collagenase to remove follicular cells and incubated in Barth's solution (in mM: 88 NaCl; 0.82 MgSO$_4$; 0.33 Ca (NO$_3$)$_2$; 0.41 CaCl$_2$; 2.4 NaHCO$_3$; 10 HEPES, pH 7.4; 200 mosmol). After 16–24 hours, oocytes were injected with about 50 nl of mRNA or water and incubated in Barth's solution with gentamicin at about 18° C. for another three days after which uptake of $^{14}$C-urea was measured.

Unlabelled urea was deionized by passing it through an ion exchange column (AG501-X8 (D), 20–50 Mesh, Bio Rad) immediately before use. The uptake solution consisted of 2 microcuries $^{14}$C-urea; 1 mM urea; 200 mM mannitol; 2 M KCl; 1 mM MgCl$_2$; 1 mM CaCl$_2$; 10 mM HEPES; and 5 mM TRIS, unless otherwise specified. In all uptake experiments oocytes were pre-incubated in uptake solution minus urea for one hour. After completion of the uptake, oocytes were washed with ice-cold wash solution (uptake solution without the labelled urea), dissolved in 10% SDS and used for scintillation counting.

Messenger RNA, fractionated as above, was collected in 0.6 ml fractions. In preliminary experiments, uptake of $^{14}$C-labelled urea (50 mM) was measured three days after injection at 5, 30 and 60 minute intervals. Poly(A)+RNA (50 ng/oocyte) from rabbit kidney medulla showed a stimulation of urea transport 3.9-fold above that of water-injected control oocytes. Phloretin at 0.25 mM inhibited the 30 minute uptake of urea by approximately 50%.

Expression experiments using *Xenopus oocytes* injected with size-fractionated poly(A)+ RNA from rabbit kidney inner medulla showed that the highest stimulation of urea transport can be obtained using a 3–4.5 kb RNA size-range. A striking observation, however, was that a lower level of transport was also induced by the 2.5 to 3 kb and the 4.5 to 5 kb RNA size-range. This suggested that messages of different sizes induce urea transport in oocytes. This was corroborated by the presence of a 3 kb band on the outer kidney medulla (See FIG. 6) as well as the complicating effect of genomic C repeats, as discussed below. High resolution RNA separation was therefore critical to the success of cloning.

The mRNA encoding the urea transporter polypeptide of the 4–4.5 kb size fraction was used to prepare a cDNA library using an in vitro expression vector.

cDNA was synthesized by the method of Gubler and Hoffman (Gene, 25: 263–269, (1983)) and Sall-Notl linkers were added according to the GIBCO BRL cDNA synthesis system. Full size cDNA was separated from partial products by electrophoresis using preparative electrophoresis according to Hediger, supra. The material was ethanol precipitated and ligated into the pSPORT1 in vitro expression vector (Gibco BRL) and the plasmid DNA transfected into *E. coli* by electroporation. About 2,000 clones were analyzed by functional expression in all szes.

Synthetic mRNA was prepared from pools of 500 clones using a modification of the method of Krieg and Melton (Nucl. Acids. Res., 12:7057–7070 (1984)). Briefly, plasmid DNA was extracted by a miniprep technique followed by Gene Clean ™ (Bio 101, Inc.) purification, and the plasmid DNA linearized with Noa and then used for in vitro transcription and capping. T7 RNA polymerase (Stratagene) was used, and the procedures were as specified by the manufacturer. RNA was purified by one phenol/chloroform extraction. Unincorporated ribonucleotides and the RNA cap structure were removed by two ethanol precipitations.

Initially, RNA (about 4 µg) was prepared from pools of clones and tested using the oocyte expression assay. Eleven pools of 500 clones were analyzed. Among these, two pools were positive. One of the two pools was subdivided into smaller pools and analyzed until a single urea transporter clone identified. This clone was called "UT1". The remaining pool was not further characterized. UT1 cRNA induced a 7.5 fold increase in 30 minute uptake of $^{14}$C-urea (50 mM) over controls. However, urea transport was not phloretin-sensitive. cDNA sequencing revealed that the UT1 cDNA sequence did not contain a large open reading frame. On high and low-stringency Northern blots of rabbit tissues (kidney, intestine, brain liver, heart, etc.) the $^{32}$P-labeled UT1-probe did not hybridize to discrete bands. Instead, smears of various intensities were observed for all tissues which covered all size-ranges (from approximately 0.5 kb to >10 kb).

A possible explanation for the unexpected properties of UT1 was obtained from a search of DNA sequences related to UT1. Searching the GenBank database reveals that UT1 cDNA is homologous to rabbit C-repeats. These repeats are similar to human Alu repeats in many respects and contain the internal control region for transcription by RNA polymerase III (J. Mol. Biol. (1984) 176, 1–20). They end in poly (dA) tracts of variable length. Both families of repeats are actively transcribed and the bulk of the transcripts are confined to the nucleus. A heterogeneous distribution of C repeat RNA sizes was found, ranging from 330 to 8,200 nucleotides and different amount of C repeats were found to accumulate in a variety of tissues. RNA from C-repeats is encoded at the 3' end of the element. There is no indication that these RNAs act as messengers. No long open reading frames beginning with ATG could be found in the individual C-repeats. C-repeats are considered to be examples of parasitic or selfish DNA. A possible explanation for the action of the UT1 C-repeat in Xenopus oocytes is that the UT1 cRNA inserts into the oocyte genome, for example in the promoter region of an endogenous oocyte urea transporter gene, and thereby stimulates the expression of phloretin-insensitive urea transport.

In an attempt to isolate a phloretin-sensitive urea transporter cDNA, the cDNA library prepared from the 4–4.5 kb RNA fraction was re-screened. Ten pools of 300 clones were analyzed. Two pools showed enhancement of urea uptake but only one pool exhibited significant phloretin-sensitivity (approximately 50% inhibition at 0.35 mM phloretin). This pool was progressively subdivided into smaller pools and cRNA (50 nl; 0.2–0.3 µg/µl) was prepared and analyzed in oocytes. A single urea transporter clone was isolated which was termed "UT2".

Proteins produced by in vitro translation are shown in FIG. 3. This yielded a protein within an apparent molecular weight of 40 kDa. This is in agreement with the expected mobility of an integral membrane protein of 397 amino acids.

B: Sequencing

The UT2 DNA (SEQ ID NO.: 1) in pSPORT plasmid (GIBCO, BRL) was sequenced according to the Sanger dideoxynucleotide chain termination method using the "Sequenase" V2.0 DNA sequencing kit (U.S. Biochemical Corp.). Oligonucleotides were synthesized by Midland Certified Reagent Co., (Midland, Tex.) and used as primers to complete sequencing.

The above example of the expression cloning of UT1 illustrates that the ability to demonstrate stimulation of urea transport in oocytes does not necessarily lead to the cloning of a urea transporter. In the above example, we ended up with a genomic repeat which somehow upregulated an endogenous oocyte transporter. We did not end up with the transporter cDNA itself. A similar problem occurred during attempts to clone a cystine transporter from rat kidney cortex (Wells and Hediger (1992) Proc. Natl. Acad. Sci. USA, 89:5596–5600). Although injection of oocytes with kidney cortex mRNA resulted in a large stimulation (>20-fold) of cystine uptake, and fractionation of mRNA resulted in the isolation of a narrow size-fraction of approximately 2.2 kb, the screening of an expression library prepared from this fraction did not result in the cloning of the cystine transporter. The screening resulted in the cloning of a transporter "activator" which stimulated the expression of an endogenous oocyte cystine transporter.

Example 2: Isolating a Human Homolog of Rabbit Urea Transporter Polypeptide

A portion of the human urea transporter gene is amplified from human kidney DNA using the polymerase chain reaction technique (Saiki, R.K., el al., 1985, Science 230 1350–1354) using NotI-SalI sites in the PCR primers. The 100 µl reaction contains 10 mM Tris-HCl pH 8.3, 50 mM KCl, 0.001% (w/v) Gelatin, 2 mM MgCl2, 200 µM dNTPs, 1.5 µM SEQ ID NO.: 1, 1.5 µM primer sequence, 2.5 units Taq Polymerase (Perkin Elmer Cetus), and 1.0 µg of human kidney DNA (obtained from a trauma victim). The DNA Thermalcycler (Perkin Elmer Cetus, Model N801) is programmed for the following incubations:

1. 94° C., 2 min. (initial denaturation)
2. 94° C., 1 min. (denaturation)
3. 50° C., 1 min. (annealing)
4. 72° C., 3 min. (elongation)
5. Steps 2–4 cycle 50 times (amplification)
6. 4° C., Soak (storage)

The DNA amplified in this reaction is electrophoresed on 5% polyacrylamide gels to verify band length. If the size is determined to be correct, the DNA is purified by phenol extraction, then digested with NotI and SalI to remove the termini. The DNA is then ligated into the NotI/SalI site of vector pUC19 (New England Biolabs). The DNA is transformed into E. coli strain DH5-alpha made competent by the $CaCl_2$ procedure (Hanahan, D., 1983, J. Mol. Biol. 155:557). The human urea transporter is then sequenced by the chain-termination method (Sanger, F. et al., 1977, Proc. Natl. Acad. Sci. USA 74:5463).

An alternate cloning procedure for genomic DNA or cDNA encoding human urea transporter polypeptide includes generating oligonucleotides from the polymerase chain reactions described above and radioactively labeling it according to the procedure described in Sambrook et al. (1989). These oligonucleotides are used to screen a λgt11 genomic library from a human kidney cell line. Alternatively, a λgt11 cDNA library prepared from mRNA from the same human kidney cell line SH-SY5Y is used. Construction of these libraries follows the procedure of Sambrook, J. et al., Molecular Cloning, (1989). Alternatively, a commercially available library, available from Clontech (Palo Alto, Calif.), can be used.

Hybridization conditions am as described by Cate et al., Cell, 45:165 (1986), except that the final wash in tetramethyl ammonium chloride is omitted. DNA inserts from positive plaques are subcloned directly into the plasmid vector pBluescript SKM13+(Stratagene, Inc. San Diego, Calif.). Positive plasmid subclones are identified by colony hybridization, with the use of the same oligonucleotide hybridization probe. Minipreparations of plasmid DNA are prepared from positive colonies.

The nucleotide sequence immediately upstream from the oligonucleotide binding site is determined by double strand sequencing (Chen and Seeburg, DNA, 4:165 1985), using $^{32}p$ end-labeled oligonucleotide as sequencing primer and nonradioactive nucleotides in the extension reactions. Subclones whose codon order upstream from the priming site match the known rabbit amino acid sequence (SEQ. ID. NO. 2) are sequenced in their entirety by the diideoxy chain termination method, with either the Klenow fragment of Escherichia coli DNA polymerase I or modified bacteriophage T7 DNA polymerase (Sequenase; United States Biochemicals) in the extension reactions. Subclones are sequenced from their termini, from both directions from a set of restriction sites. Clones are obtained whose codon order is at least partially similar to the amino acid sequence of rabbit urea transporter polypeptide. A full-length genomic or cDNA sequence for human urea transporter is assembled from overlapping partial clones.

Example 3: Targeted Gene Walking as a Means of Cloning Urea Transporter Polypeptide Targeted gene walking (TGW) is a modification of a standard polymerase chain reaction (PCR) that allows amplification of unknown DNA sequences adjacent to short segments of known sequence. Parker, et al., Nucl. Acids Res., 19:3055, (1991). Unlike conventional PCR techniques that amplify DNA sequences between two known primer sites, TGW can amplify DNA adjacent to one such site. Thus, TGW can serve as a replacement for conventional cloning and library screening methods for isolating sequences upstream or downstream from known sequences. The procedure can be used to isolate genes from any starting DNA template for which a limited amount of sequence information is known.

First, several standard PCR reactions are run in parallel using one "targeted primer" and different "walking primers." The targeted primer is a sequence-specific primer exactly complementary to a known sequence on the DNA molecule of interest, and is directed toward unknown adjacent sequences. The walking primers are nonspecific sequences not complementary to DNA near the target primer. The walking primers can be any oligonucleotides unrelated to the target primer sequence. In the first series of PCRs, products are produced only when a walking primer anneals to a DNA strand contiguous with and complementary to the strand to which the targeted primer has hybridized. The PCR products of interest are preferably within the 5 kilobase size range. Amplification products are produced with as many as 60% mismatched nucleotides within the walking primer relative to DNA template. Perfect base-pairing is required only for the first two 3' nucleotides of the walking primer, but partial homology is tolerated otherwise. Annealing temperature is a key variable in determining the number of PCR products, as identified by agarose gel electrophoresis.

Second, an oligomer extension assay is performed using an "internal detection primer." This primer represents known sequences between the previous two primers, contiguous with the targeted primer. The internal detection primer is kinased with $^{32}P$-gamma-ATP, then used in a single PCR cycle with DNA from the first PCR as template. This extension identifies products in the first PCR contiguous with the targeted primer. These new products are identified by agarose gel electrophoresis and autoradiography. Any products that do not hybridize to the internal detection primer represent non-contiguous amplification products produced by any subset of the primers.

Lastly, bands identified in the oligomer extension assay are excised from the gel, and reamplified by standard PCR using target primer and the walking primer that produced the band initially. This new PCR band is then sequenced directly to provide previously unknown sequence information.

To extend information in the opposite direction, complements are made of the targeted and internal detection primers, and their order is reversed in the protocol.

Figure 4:
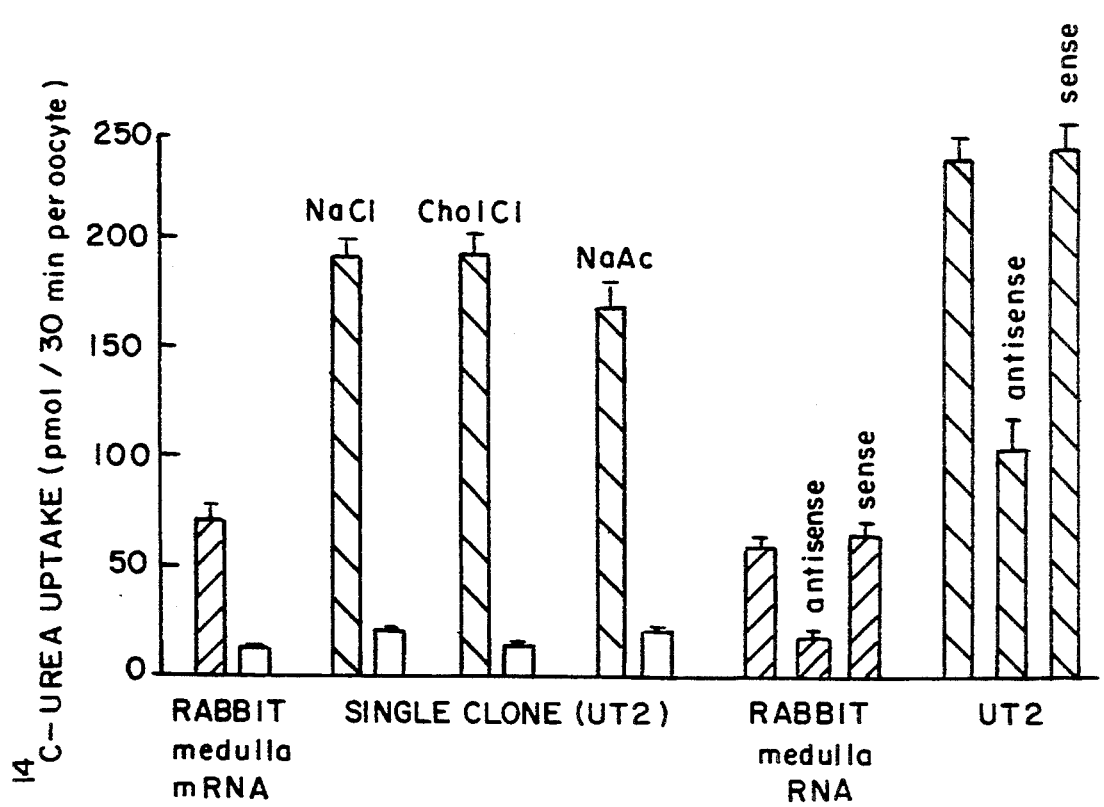
FIG. 4 illustrates $^{14}$C-urea (1 mM) uptake into Xenopus oocytes and the effect of various manipulations of uptake conditions on urea transport. Each column is the mean± s.e.m. (n=6-8 oocytes). Cross-hatched columns show uptake into oocytes injected with poly (A)+ RNA from rabbit kidney medulla. Solid columns show uptake into oocytes injected with in vitro transcribed urea transporter cDNA ("UT2"). Open bars show uptake by oocytes injected with water.

Example 4: Facilitation of Urea Uptake by Urea Transporter Polypeptide and other Compounds Urea transport in the mammalian kidney is generally considered to be passive, although there is some evidence for active ion coupled transport. In studies addressing ion dependencies, urea uptake was measured in oocytes injected with urea transporter cRNA, as described above in Example 1. In the incubation solution, however, mannitol was replaced by NaCl (100 mM), choline chloride (100 mM) or sodium acetate (100 mM). Replacing mannitol with NaCl did not alter urea uptake (FIG. 4). Replacement of mannitol with choline chloride or sodium acetate also had no effect, indicating that urea transport is not coupled to Na$^-$ or Cl$^-$.

Electrophysiological studies are in agreement with this finding. Electrophysiological measurements were made on oocytes 3–4 days after injection with urea transporter cRNA-injected oocytes using conventional two-microelectrode voltage clamp methods (Axoclamp-2A, Axon Instruments). Membrane current was measured in a standard bath of 96 mM NaCl; 2 mM KCl; 1.8 mM CaCl$_2$; 1.0 mM MgCl$_2$; and 5 mM HEPES, pH 7.4, at a holding potential of −60 mV. Bath applied urea (1 and 100 mM) did not evoke a significant current indicating that urea transport is electroneutral (data not shown).

Uptake of $^{14}$C-urea (1 mM) into urea transporter cRNA-injected oocytes reached a maximum value of approximately 250 pmoles/oocyte between 10 and 30 minutes. If the effective cytoplasmic volume of an oocyte is assumed to be 0.25 l, 250 pmoles/oocyte corresponds to an intracellular urea concentration of 1 mM. Thus, after 10 minutes, $^{14}$C-urea had almost completely equilibrated across the oocyte plasma membrane. From this data we conclude that transport of urea is via facilitated transport. The calculated value for the urea permeability of urea transporter-injected oocytes based on initial rates of uptake is $4.5 \times 10^{-5}$ cm/sec. This is in agreement with the published value for in vitro perfused terminal IMCD which is between 11.6 to $13.1 \times 10^{-5}$ cm/sec. In contrast, the permeability of water-injected control oocytes for urea is $1.9 \times 10^{-6}$ cm/sec, a value characteristic of lipid-phase permeation of urea. Thus, urea transporter increased the permeability of oocytes to urea 23-fold.

For hybrid depletion studies, rabbit kidney medulla poly (A)+ RNA or urea transporter cRNA (0.9 μg/μl, heat-denatured) was incubated with antisense or sense oligonucleotides (0.3 μg/μl) corresponding to a region 21 nucleotides downstream from the start codon (nucleotides in SEQ ID NO.: 1 ) in the presence of 50 mM NaCl at 42° C. for 20 minutes and then cooled on ice and injected into oocytes. Oocytes were incubated at 18° C. for three days after which uptake of $^{14}$C-urea is measured. A 30 minute uptake of 1 mM urea was reduced by about 67% whereas incubation with a sense oligonucleotide corresponding to the same region had no significant effect on uptake (FIG. 4). This is supported by the observation that the reduction in uptake after depletion with urea transporter cRNA with antisense oligonucleotide is incomplete (55% reduction; see FIG. 4).

To study the uptake inhibition by phloretin, phloretin (Sigma) was dissolved in ethanol at 0.5M and added to the uptake solution to give the desired final concentration of 0.35 mM and 0.70 mM. The concentration of ethanol was no more than 0.1%. Ethanol at the same concentration is added to uptake solution without phloretin. Following 15 min pre-incubation in phloretin, $^{14}$C-urea was added and urea flux was then measured during 90 seconds. Phloretin inhibited urea transporter-facilitated urea uptake. Inhibition of urea uptake (1.0 mM urea) was 48% with 0.35 mM phloretin and 78% with 0.7 mM phloretin (data not shown).

For inhibition studies using urea analogues, all analogues were deionized as described in Example 1 immediately before use. Uptake of $^{14}$C-urea (1 mM) in the presence of 150 mM of the urea analogues thiourea, N-methylurea, 1,3-dimethylurea, acetamide or 1,1,-dimethylurea is shown in FIG. 5. Of the analogues tested, 1,3 dimethylurea effectively inhibited urea transport by 65%. Thiourea and N-methylurea reduced uptake to a lesser degree (by 38%) and acetamide and 1,1-dimethylurea had no significant effect. This qualitative pattern of inhibition is identical to that of apical vasopressin-sensitive urea transport previously shown in in vitro rat kidney IMCD. Chou and Knepper, 257 Am. J. Physiol. F359-365 (1989).

Urea transporter polypeptide of the invention has three potential phosphorylation sites, two PKA sites (Ser 31 and 386) and a PKC site (Ser 13) (SEQ ID NO. 2). In this regard, facilitation of urea transport by vasopressin is believed to result from the occupation of V2-type vasopressin receptors followed by activation of adenylate cyclase and an increase in intracellular cAMP levels. Star, R.A. et al., Clin. Invest., 81:1879-1888 (1988). In vitro studies suggest that facilitation of urea transport by vasopressin elicits an increase in the number of functional transporters in the apical membrane. Chou, C.L. and M.A. Knepper, Am. J. Physiol., 257, supra.

It is possible that facilitation of urea transport by vasopressin is the result of direct phosphorylation of the transporter or of recruitment of functional transporters from intracellular vesicle pools. Since Xenopus oocytes do not have V2-type vasopressin receptors, we tested the former hypothesis we studied the effect of several cAMP agonists on urea transporter-facilitated urea uptake in oocytes. The cAMP analogues Sp-cAMPS, dibutyryl cyclic-AMP or 8-bromo-cAMP (30 minute preincubation, 1 mM per analogue) have no effect on urea transporter-facilitated urea transport (data not shown). These are two possible explanations for this finding: (a) stimulation involves recruitment of transporters from vesicle pools but this mechanism does not function in Xenopus oocytes; (b) stimulation involves direct phosphorylation but additional stimulation using cAMP analogues is not effective because the transporter is already fully phosphorylated. This is consistent with the observation that oocytes have high intracellular levels of cAMP and protein kinase (PKA) activity.

Example 4: Urea Transport Kinetics

Saturation of transport with increasing substrate concentration is a characteristic feature of carrier-mediated transport. The maximal urea concentration which can be used with oocytes is approximately 200 mM. Urea transport in IMCD (perfused tubules) and erythrocytes, however, has $K_m$ values for urea which are significantly above 200 mM. Our results demonstrated that there was no saturation of urea transporter polypeptide-mediated urea transport in the concentration range between 1 and 200 mM urea. Thus, the present urea transporter polypeptide also has a low affinity for urea. An alternative explanation is that urea transporter-facilitated urea transport does not exhibit saturation kinetics at all. This would indicate that the present urea transporter is not actually a true transporter but is rather a channel or pore through which, upon stimulation by vasopressin, urea can freely diffuse. This process would be distinct from a transporter which usually requires binding of the substrate to the transporter surface and undergoes a conformational change followed by translocation of the substrate to the other side of the membrane. The present urea transporter may actually represent a transitional form between a transporter and a channel.

Example 5: Tissue Distribution of Urea Transporter Polypeptide

Low and high stringency Northern analysis of poly (A)+RNA from rabbit tissues was probed with $^{32}$P-labelled urea transporter polypeptide eDNA (SEQ ID NO. 1). After electrophoresis of poly (A+) RNA (3 μg/lane) in a 1% formaldehyde/agarose gel, the RNA was blotted onto a nitrocellulose filter (Schleicher & Schuell). The filter was hybridized at 35° C. (low stringency) and 42° C. (high stringency) in 50% formamide, using the $^{32}$P-labeled full-length sequence as a probe. The probe was labeled using the T7 QuickPrimer Kit (Pharmacia). The filter was washed in 0.1X SSC/0.1% SDS at 42° C. (low stringency) and 65° C. (high stringency). RNA from spleen of rabbit and mouse treated with acetylphenyl hydrazine was kindly provided by Dr. Seth Alper (Molecular Medicine Unit, Beth Israel Hospital).

A strong band of size 4 kb was detected in colon, kidney inner medulla, papilla and two bands of approximately 3 kb were also detected in the outer medulla (FIG. 6). At low stringency, the probe also hybridized weakly to 4 kb band in RNA from liver and lung (FIG. 6). Total RNA was used for papilla, which explains the slightly weaker band as compared to inner medulla. The last two lanes in FIG. 6 represent RNA from spleen from anemic (acetylphenyl hydrazine-treated) rabbits or mice (see asterisks). No signal was detected in these lanes, indicating that the erythrocyte urea transporter is different from the urea transporter of the present invention. An explanation of the discrepancy between the message sizes in kidney inner medulla, papilla and colon, and the size of urea transporter cDNA (3.1 kb) is that the cDNA synthesis may have been primed at an internal poly (A) stretch.

In situ hybridization of rabbit kidney was performed as previously described using 4% paraformaldehyde-fixed tissue sections (approximately 7 μm thickness). Briefly, $^{35}$S-labeled sense and antisense RNA probes were synthesized from the full length clone (in pSPORT) after linearization of plasmid DNA with HindIII or KpnI, using T7 or SP6 RNA polymerase, respectively. RNA probes were hydrolyzed for 50 min to form probes of 100 nucleotides approximately. The probes were hybridized to tissue sections at 50° C. oven-tight in hybridization solution containing 50% formamide. Sections were washed in 5xSSC for 30 min at 50° C., in 50% formamide and 2xSSC for 20 min at 50° C. and then twice in 0.4M NaCl for 20 min at 37° C. After the sections were treated with RNase A and RNase TI at 37° C. for 30 min and washed in 0.1xSSC at 37° C. for 15 min, they were dipped into Kodak NTB2 emulsion and developed 6 days later. Counterstaining was performed with haematoxylin-eosin. Control experiments with $^{35}$S-labelled sense cRNA were performed to validate the specificity of the signal observed with the antisense probe.

Localization of the urea transporter polypeptide message using in situ hybridization of rabbit kidney perfused with 4% paraformaldehyde revealed, in a parasagital section of rabbit kidney, a strong signal for urea transporter cRNA probe in the terminal part of the IMCD and the papilla (FIG. 7a). A specific signal was also observed in the inner stripe of the outer medulla (FIG. 7b). A urea transporter polypeptide signal of the inner medulla showing a cross-section of IMCD is illustrated in FIG. 7c. A closeup of the papillary region is shown in FIG. 7d. Junctions between converging collecting ducts in the inner medulla are clearly visible. (Abbreviations: C, cortex; OM, outer medulla, IM, inner medulla; P, papilla).

Example 6: Expression of Urea Transporter Polypeptide.

The following method for transient expression of urea transporter polypeptide cDNA in cultured cells is adapted from Birnir et al., supra.

COS-7 cells, or other cultured cells such as CHO cells, are used. COS-7 cells, derived from simian kidney, may synthesize renal membrane proteins more efficiently than amphibian oocytes. Tissue culture medium, serum, and antibiotics are obtained from GIBCO (Gaithersburg, Md.).

The eukaryotic expression vector pEUK-C1 is obtained from Clontech (Palo Alto, Calif.). Plasmid pEUK-UT2 is constructed by inserting SEQ ID NO.: 1 cDNA (blunt-ended with T4 DNA polymerase) into the SmaI side of plasmid pEUK-C1. The orientation and correct insertion at the 5' end is confirmed by DNA sequencing. pEUK-UT2 (15 μg) is transfected into COS-7 cells using lipofectin. Briefly, COS-7 cells are seeded onto 35 mm tissue culture plates (Falcon, N.J.) in Dulbecco's modified Eagle's medium (DMEM) with 10% fetal bovine serum and 1% antimycotic (containing Fungizon-GIBCO) and transfected at a confluency of 80–95%. Immediately before transfection, cell monolayers are washed twice with OPTI-MEM I medium (GIBCO). For each 35 mm plate, 15 μg of plasmid and 15 μg of Lipofectin are mixed for 30 min in 0.5 ml of OPTI-MEM I medium and then added to the plate.

After incubation for 24 h at 37° C. in a humidified atmosphere containing 5% $CO_2$: 1 ml of DMEM with 10% serum is added. Uptake of $^{14}$C-urea is measured 48 to 72 h post-transfection. The plates are incubated in a 280 mM mannitol solution containing 2 mM KCl, 1 mM $CaCl_2$, 1 mM $MgCl_2$: 10 mM HEPES, and 5 mM TRIS, with and without cyclic AMP analogues such as 8-Bromo cAMP (1 mM). After this, about 0.75 ml of uptake solution containing 2 microcuries $^{14}$C-urea per plate (1 mM urea final concentration), 280 mM mannitol, 2 mM KCl, 1 mM $CaCl_2$, 1 mM $MgCl_2$, 10 mM HEPES, and 5 mM TRIS is added. After 1 minute, the uptake is stopped by aspirating off the uptake solution and rapidly washing the plate with ice-cold washing solution (1 mM urea, 280 mM mannitol, 2 mM KCl, 1 mM $CaCl_2$, 1 mM $MgCl_2$, 10 mM HEPES, and 5 mM TRIS). The cells are solubilized in 0.2 M NaOH and aliquoted for liquid scintillation counting. The protein concentration is determined using the dye-binding procedure of Bradford, Anal. Biochem. 72:248–254 (1976).

In control experiments, pEUK-Cl plasmid DNA without SEQ ID NO.: 1 is transfected. The transfection efficiency is monitored after co-transfection with plasmid pCH110 (Clontech), containing a functional Lac Z gene and a SV 40 origin of replication. COS-7 cells produce the SV 40 large tumor antigen which allows replication of plasmids (such as pCH110 and pEUK-Cl) containing a SV 40 origin. The product of the Lac Z gene, beta-galactosidase, is measured using X-Gal. Generally, between 15–25% of cells are transfected.

Example 7: Preparation of Constructions for Transfections and Microinjections

Methods for purification of DNA for microinjection are well known to those of ordinary skill in the art. See, for example, Hogan et al., *Manipulating the Mouse Embryo*, Cold spring Harbor Laboratory, Cold Spring Harbor, N.Y. (1986); and Palmer et al., *Nature*, 300:611 (1982).

Construction of Transgenic Animals

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci, USA*, 82:4438–4442 (1985)). Embryos can be infected with viruses, especially retroviruses, modified to bear urea transporter genes of the invention.

Pluripotent stem cells derived from the inner cell mass of the embryo and stabilized in culture can be manipulated in culture to incorporate urea transporter genes of the invention. A transgenic animal can be produced from such cells through implantation into a blastocyst that is implanted into a foster mother and allowed to come to term.

Animals suitable for transgenic experiments can be obtained from standard commercial sources such as Charles River (Wilmington, Mass.), Taconic (Germantown, N.Y.), Harlan Sprague Dawley (Indianapolis, Ind., etc. Swiss Webster female mice are preferred for embryo retrieval and transfer. B6D2F$_1$ males can be used for mating and vasectomized Swiss Webster studs can be used to stimulate pseudopregnancy. Vasectomized mice and rats can be obtained from the supplier.

Microinjection Procedures

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia*, 47:897–905 (1991). Other procedures for introduction of DNA into tissues of animals are described in U.S. Pat. No., 4,945,050 (Sanford et al., Jul. 30, 1990).

Transgenic Mice

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by CO: asphyxiation or cervical dislocation and embryos are recovered from excised oviducts and placed in Dulbecco's phosphate buffered saline (DPSS) with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The pipet tip is inserted into the infundibulum and the embryos transferred. After the transfer, the incision is closed by two sutures.

Transgenic Rats

The procedure for generating transgenic rats is similar to that of mice See Hammer et al,, *Cell,* 63:1099–1112 (1990). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPSS with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10–12 embryos are transferred into each rat oviduct through the infundibulum. The incision is then closed with sutures, and the foster mothers are housed singly.

Embryonic Stem (ES) Cell Methods

Introduction of DNA into ES cells:

Methods for the culturing of ES cells and the subsequent production of transgenic animals by the introduction of DNA into ES cells using methods such as electroporation, calcium phosphate/DNA precipitation; and direct injection are well known to those of ordinary skill in the art. See, for example, Teratocarcinomas and Embryonic Stem Cells, A Practical Approach, E.J. Robertson, ed., IRL Press (1987). Selection of the desired clone of thrombospondin-4-containing ES cells is accomplished through one of several means. Although embryonic stem cells are currently available for mice only, it is expected that similar methods and procedures as described and cited here will be effective for embryonic stem cells from different species as they become available.

In cases involving random gene integration, a clone containing the urea transporter gene of the invention is co-transfected with a gene encoding neomycin resistance. Alternatively, the gene encoding neomycin resistance is physically linked to the urea transporter gene. Transfection is carried out by any one of several methods well known to those of ordinary skill in the art (E.J. Robertson, supra). Calcium phosphate/DNA precipitation, direct injection, and electroporation are the preferred methods. Following DNA introduction, cells are fed with selection medium containing 10% fetal bovine serum in DMEM supplemented with G418 (between 200 and 500 µg/ml biological weight). Colonies of cells resistant to G418 are isolated using cloning rings and expanded. DNA is extracted from drug resistant clones and Southern blotting experiments using a transgene-specific DNA probe are used to identify those clones carrying the urea transporter sequences. In some experiments, PCR methods are used to identify the clones of interest.

DNA molecules introduced into ES cells can also be integrated into the chromosome through the process of homologous recombination. Copecchi, *Science*, 244:1288–1292 (1989). Direct injection results in a high efficiency of integration. Desired clones are identified through PCR of DNA prepared from pools of injected ES cells. Positive cells within the pools are identified by PCR subsequent to cell cloning. DNA introduction by electroporation is less efficient and requires a selection step. Methods for positive selection of the recombination event (i,e., neo resistance) and dual positive-negative selection (i.e., neo resistance and gancyclovir resistance) and the subsequent identification of the desired clones by PCR have been described by Copecchi, supra and Joyner et al., *Nature*, 338:153–156 (1989), the disclosures of which are incorporated herein.

Embryo Recovery and ES Cell Injection:

Naturally cycling or superovulated female mice mated with males are used to harvest embryos for the implantation of ES cells. It is desirable to use the C57BL165 strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10–20 ES cells are injected into blastocysts using a glass microneedle with an internal diameter of approximately 20

Transfer of Embryos to Receptive Females:

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

Identification of Transgenic Mice and Rats

Tail samples (1–2 cm) are removed from three week old animals. DNA is prepared and analyzed by Southern blot or PCR to detect transgenic founder ($F_0$) animals and their progeny ($F_1$ and $F_2$). In this way, animals that have become transgenic for the desired urea transporter genes are identified. Because not every transgenic animal expresses the urea transporter poly polypeptide, and not all of those that do will have the expression pattern anticipated by the experimenter, it is necessary to characterize each line of transgenic animals with regard to expression of the urea transporter polypeptide in different tissues.

Production of Non-Rodent Transgenic Animals

Procedures for the production of non-rodent mammals and other animals have been discussed by others. See Houdebine and Chourrout, Supra; Pursel et al., *Science* 244:1281–1288 (1989); and Simms et al., Bio/Technology, 6:179–183 (1988).

Identification of Other Transgenic Organisms

An organism is identified as a potential transgenic by taking a sample of the organism for DNA extraction and hybridization analysis with a probe complementary to the urea transporter gene of interest. Alternatively, DNA extracted from the organism can be subjected to PCR analysis using PCR primers complementary to the urea transporter gene of interest.

Example 8: Protocol for Inactivating the Urea Transporter Gene.

Mouse genomic clones are isolated by screening a genomic library from the D3 strain of mouse with a rabbit urea transporter probe. Duplicate lifts are hybridized with a radiolabeled probe by established protocols (Sambrook, J. et al., *The Cloning Manual*, Cold Spring Harbor Press, N.Y.). Plaques that correspond to positive signal on both lifts are isolated and purified by successive screening rounds at decreasing plaque density. The validity of the isolated clones is confirmed by nucleotide sequencing.

The genomic clones are used to prepare a gene targeting vector for the deletion of urea transporter in embryonic stem cells by homologous recombination. A neomycin resistance gene (neo) with its transcriptional and translational signals, is cloned into convenient sites that are near the 5' end of the gene. This will disrupt the coding sequence of urea transporter and allow for selection by the drug Geneticin (G418) by embryonic stem (ES) cells transfected with the vector. The Herpes simplex virus thymidine kinase (HSV-tk) gene is placed at the other end of the genomic DNA as a second selectable marker. Only stem cells with the neogene will grow in the presence of this drug.

Random integration of this construct into the ES genome will occur via sequences at the ends of the construct. In these cell lines, the HSV-tk gene will be functional and the drug gancyclovir will therefore be cytotoxic to cells having an integrated sequence of the mutated urea transporter coding sequence.

Homologous recombination will also take place between homologous DNA sequences of the ES urea transporter genome and the targeting vector. This usually results in the excision of the HSV-tk gene because it is not homologous with the urea transporter gene.

Thus, by growing the transfected ES cells in G418 and gancyclovir, the cell lines in which homologous recombination has occurred will be highly enriched.

These cells will contain a disrupted coding sequence of urea transporter. Individual clones are isolated and grown up to produce enough cells for frozen stocks and for preparation of DNA. Clones in which the urea transporter gene has been successfully targeted are identified by Southern blot analysis. The final phase of the procedure is to inject targeted ES cells into blastocysts and to transfer the blastocysts into pseudopregnant females. The resulting chimetic animals are bred and the offspring are analyzed by Southern blotting to identify individuals that carry the mutated form of the gene in the germ line. These animals will be mated to determine the effect of urea transporter deficiency on murine development and physiology.

Equivalents

It should be understood that the preceding is merely a detailed description of certain preferred embodiments. It therefore should be apparent to those skilled in the art that various modifications and equivalents can be made without departing from the spirit or scope of the invention.

What is claimed is:

1. An isolated nucleic acid comprising SEQ ID NO.: 1, wherein said isolated nucleic acid sequence, when expressed in a cell, is capable of facilitating urea transport across a membrane of said cell in a manner that is inhibitable by phloretin, inhibitable by a urea analogue, and substantially independent of sodium ion and chloride ion concentrations, said sequence encoding a polypeptide that is a urea transporter polypeptide of apparent molecular weight on SDS-PAGE of about 40 kDA in non-glycosylated form and at least 45 kDA in glycosylated form, said urea transporter polypeptide having at least two hydrophobic domains at least 75 amino acids in length, each hydrophobic domain lacking any interspersed hydrophilic domain.

2. The isolated nucleic acid sequence of claim 1, the sequence originating in mammalian tissue selected from the group consisting of mammalian renal papillary tip, mammalian renal medulla, and mammalian colon.

3. A recombinant vector containing the isolated nucleic acid sequence of claim 1.

4. A host transformed by the recombinant vector of claim 3.

5. A method for producing a urea transporter polypeptide comprising:
   culturing the transformed host of claim 4 under conditions sufficient for the expression of the urea transporter polypeptide;
   recovering the urea transporter polypeptide; and
   purifying the urea transporter polypeptide.

6. An isolated nucleic acid sequence that is a degenerate sequence of SEQ ID NO. 1, wherein at least one codon of SEQ ID NO.:1 is substituted by a different codon, said at least one codon and said different codon encoding the identical amino acid residue, wherein said degenerate sequence, when expressed in a cell, is capable of facilitating urea transport across a membrane of said cell in a manner that is inhibitable by phloretin, inhibitable by a urea analogue, and substantially independent of sodium ion and chloride ion concentrations, said degenerate sequence encoding a urea transporter polypeptide having an apparent molecular weight on SDS-PAGE of about 40 kDA in nonglycosylated form and at least 45 kDA in glycosylated form, said urea transporter polypeptide having at least two hydrophobic domains at least 75 amino acids in length, each hydrophobic domain lacking any interspersed hydrophilic domain.

7. The isolated nucleic acid sequence of claim 6 that is a fully degenerate sequence, wherein every codon of SEQ ID NO.: 1 is substituted by a different codon, said every codon and said substituted codon capable of encoding the identical amino acid.

8. An isolated nucleic acid encoding a polypeptide having a sequence comprising SEQ ID NO.: 2.

9. A recombinant vector containing the isolated nucleic acid sequence of claim 8.

* * * * *

UNITED STATES PATENT AND TRADEMARK OFFICE
CERTIFICATE OF CORRECTION

PATENT NO. : 5,441,875
DATED : August 15, 1995
INVENTOR(S) : Matthias A. Hediger It is certified that error appears in the above-indentified patent and that said Letters Patent is hereby corrected as shown below:

Column 3, line 25: please delete "eDNA"; and insert therefor -- cDNA --.

Column 3, line 31: please delete "500 m"; and insert therefor -- 500$\mu$m --.

Column 9, line 6: please delete "$^{32}$p,"; and insert therefor -- $^{32}$P, --.

Column 12, line 37: please delete "Expression"; and insert therefor -- E. Expression --.

Column 18, line 8: please delete "neogene"; and insert therefor -- neo gene --.

Column 19, line 42: please delete "micro flora"; and insert therefor -- microflora --.

Column 23, line 54: please delete "am"; and insert therefor -- are --.

Column 23, line 67: please delete "$^{32}$p"; and insert therefor -- $^{32}$P --.

Column 25, line 36: please delete "0.25 l,"; and insert therefor -- 0.25 $\mu$l --
Column 27, line 20: please delete "eDNA"; and insert therefor -- cDNA --.

UNITED STATES PATENT AND TRADEMARK OFFICE
CERTIFICATE OF CORRECTION

PATENT NO. : 5,441,875
DATED : August 15, 1995
INVENTOR(S) : Matthias A. Hediger, It is certified that error appears in the above-indentified patent and that said Letters Patent is hereby corrected as shown below:

Column 27, line 60: please delete "oven-"; and insert therefor -- over- --.

Column 27, line 61: please delete "tight"; and insert therefor -- night --.

Column 28, line 50: please delete "$CO_2$:"; and insert therefor -- $CO_2$, --.

Column 30, line 20: please delete "Transgenic".

Column 30, line 21: please add -- Transgenic-- before Rats.

Column 31, line 52: please delete "20."; and insert therefor -- 20 $\mu$m.--.

Signed and Sealed this

Twenty-fourth Day of October, 1995

Attest:

BRUCE LEHMAN

*Attesting Officer*   *Commissioner of Patents and Trademarks*